(12) United States Patent
Kaveh et al.

(10) Patent No.: US 11,857,230 B2
(45) Date of Patent: Jan. 2, 2024

(54) MAXILLARY EXPANDER AND PROTRACTION DEVICE

(71) Applicant: Facegenics Inc., Bell Canyon, CA (US)

(72) Inventors: Cameron Kaveh, Bell Canyon, CA (US); Richard Beranek, Ottawa (CA)

(73) Assignee: Facegenics, Inc., Bell Canyon, CA (US)

( * ) Notice: Subject to any disclaimer, the term of this patent is extended or adjusted under 35 U.S.C. 154(b) by 48 days.

(21) Appl. No.: 16/765,805

(22) PCT Filed: Nov. 24, 2018

(86) PCT No.: PCT/US2018/062403
§ 371 (c)(1),
(2) Date: May 20, 2020

(87) PCT Pub. No.: WO2019/104255
PCT Pub. Date: May 31, 2019

(65) Prior Publication Data
US 2020/0383710 A1    Dec. 10, 2020

Related U.S. Application Data

(63) Continuation-in-part of application No. 16/115,564, filed on Aug. 29, 2018, now Pat. No. 10,575,926.
(Continued)

(51) Int. Cl.
*A61B 17/80*  (2006.01)
*A61B 17/66*  (2006.01)
*A61B 17/86*  (2006.01)

(52) U.S. Cl.
CPC ........ *A61B 17/8071* (2013.01); *A61B 17/663* (2013.01); *A61B 17/8023* (2013.01); *A61B 17/863* (2013.01)

(58) Field of Classification Search
CPC .................................................. A61B 17/8071
See application file for complete search history.

(56) References Cited

U.S. PATENT DOCUMENTS

| 415,829 A | 11/1889 | Angle |
| 664,412 A | 12/1900 | Knapp |

(Continued)

FOREIGN PATENT DOCUMENTS

| DE | 601 20 845 | 1/2007 |
| EP | 1175874 | 1/2002 |

(Continued)

OTHER PUBLICATIONS

International Search Report and Written Opinion dated Oct. 22, 2018 for PCT application No. PCT/US2018/042200.
(Continued)

*Primary Examiner* — Olivia C Chang
(74) *Attorney, Agent, or Firm* — EVAN LAW GROUP LLC

(57) ABSTRACT

A medical device and method of expanding the maxilla of a patient via application of intra-orally generated forces and/or applying externally generated protraction forces to the maxilla of the patient is provided. The medical device can embody multiple configurations device that include skeletal anchorage device alone or in combination with a fixed aligner or an adjustable aligner.

20 Claims, 39 Drawing Sheets

Related U.S. Application Data

Figure 1A:
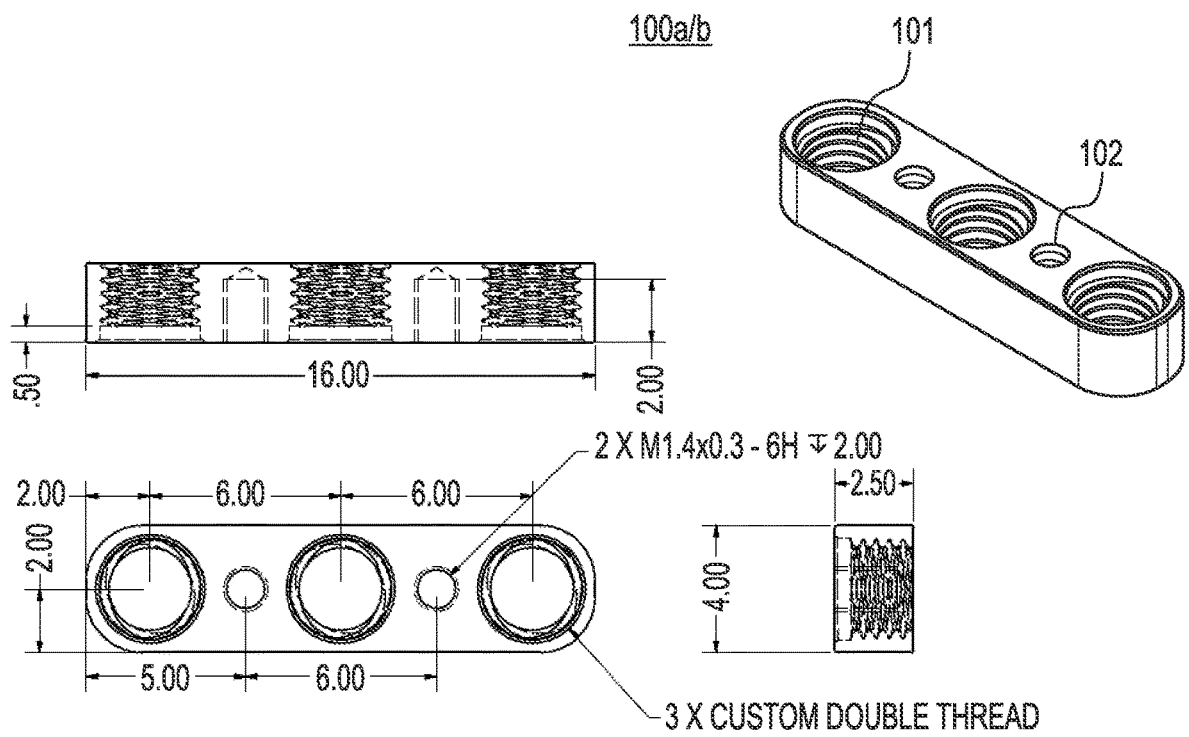

(60) Provisional application No. 62/699,264, filed on Jul. 17, 2018, provisional application No. 62/685,801, filed on Jun. 15, 2018, provisional application No. 62/676,969, filed on May 26, 2018, provisional application No. 62/590,363, filed on Nov. 24, 2017.

(56) References Cited

U.S. PATENT DOCUMENTS

| | | | |
|---|---|---|---|
| 3,303,566 | A | 2/1967 | Winkler |
| 3,391,693 | A | 7/1968 | Georgiade |
| 3,866,322 | A | 2/1975 | Broussard et al. |
| 3,977,082 | A | 8/1976 | Siatkowski |
| 4,695,250 | A | 9/1987 | Mariol |
| 4,815,972 | A | 3/1989 | Howe |
| 4,848,368 | A | 7/1989 | Kronner |
| 5,564,920 | A | 10/1996 | Klapper et al. |
| 5,695,332 | A | 12/1997 | Samuels |
| 5,885,290 | A | 3/1999 | Guerrero et al. |
| 5,890,891 | A | 4/1999 | Doyle |
| 5,902,304 | A | 5/1999 | Walker et al. |
| 5,904,479 | A | 5/1999 | Staples |
| 6,213,765 | B1 | 4/2001 | Standerwick et al. |
| 6,328,745 | B1 | 12/2001 | Ascherman |
| 8,529,579 | B2 | 9/2013 | Bulloch et al. |
| 8,640,710 | B2 | 2/2014 | Matthews |
| 8,662,889 | B2 | 3/2014 | Baker |
| 9,333,053 | B2 | 5/2016 | Alyami |
| 9,351,810 | B2 | 5/2016 | Moon |
| 10,166,089 | B2 | 1/2019 | Kahn et al. |
| 10,357,341 | B2 | 7/2019 | Alruhaimi |
| 10,575,926 | B2 | 3/2020 | Kaveh et al. |
| 10,918,463 | B1 | 2/2021 | Alruhimi |
| 2002/0156485 | A1 | 10/2002 | Sellers et al. |
| 2003/0050641 | A1 | 3/2003 | Mommaerts |
| 2003/0097137 | A1 | 5/2003 | Schendel |
| 2003/0138755 | A1 | 7/2003 | Tremont |
| 2005/0021045 | A1 | 1/2005 | Schendel |
| 2005/0256526 | A1* | 11/2005 | Johnston .............. A61B 17/663 606/90 |
| 2006/0200146 | A1 | 9/2006 | Doubler et al. |
| 2007/0287900 | A1 | 12/2007 | Breen et al. |
| 2008/0173313 | A1 | 7/2008 | Brady |
| 2009/0130620 | A1 | 5/2009 | Yazdi et al. |
| 2011/0143300 | A1 | 6/2011 | Villaalba |
| 2011/0230885 | A1 | 9/2011 | Weiner et al. |
| 2011/0277774 | A1 | 11/2011 | Connell |
| 2012/0247490 | A1 | 10/2012 | Matthews |
| 2012/0277749 | A1 | 11/2012 | Mootien et al. |
| 2013/0252195 | A1 | 9/2013 | Popat |
| 2014/0186788 | A1 | 7/2014 | Sheibani Nia et al. |
| 2015/0056566 | A1 | 2/2015 | Moon |
| 2015/0230831 | A1 | 8/2015 | Altarac et al. |
| 2015/0238228 | A1 | 8/2015 | Langenfeld |
| 2016/0270883 | A1 | 9/2016 | Yousefian |
| 2016/0270884 | A1 | 9/2016 | Yousefian |
| 2017/0281315 | A1 | 10/2017 | Sotiropoulos |
| 2018/0008376 | A1 | 1/2018 | Scommegna |
| 2018/0028282 | A1 | 2/2018 | Kahn et al. |
| 2018/0132978 | A1 | 5/2018 | Alruhaimi |
| 2018/0311014 | A1 | 11/2018 | Yousefian |
| 2018/0368945 | A1 | 12/2018 | Moon |
| 2019/0159873 | A1 | 5/2019 | Kaveh et al. |
| 2020/0297388 | A1 | 9/2020 | Kaveh |
| 2020/0383710 | A1 | 12/2020 | Kaveh |
| 2020/0405449 | A1 | 12/2020 | Kaveh |
| 2021/0275226 | A1 | 9/2021 | Kaveh et al. |

FOREIGN PATENT DOCUMENTS

| | | |
|---|---|---|
| JP | 2005-204987 | 8/2005 |
| JP | 2017-104417 | 6/2017 |
| KR | 20090068775 | 7/2009 |
| KR | 20110011225 | 2/2011 |
| KR | 10-2011-0126318 | 11/2011 |
| KR | 20160133921 | 11/2016 |
| KR | 10-2017-0066389 | 12/2018 |
| KR | 10-2018-0130375 | 12/2018 |
| WO | 2005/009260 | 2/2005 |
| WO | 2008/011698 | 1/2008 |
| WO | 2016/185018 | 11/2016 |
| WO | 2019/018249 | 1/2019 |
| WO | 2019/104255 | 5/2019 |
| WO | 2019/178008 | 9/2019 |
| WO | 2020/014648 | 1/2020 |

OTHER PUBLICATIONS

International Search Report and Written Opinion dated May 6, 2019 for PCT application No. PCT/US2018/062403.
Moon, W., "Class III treatment by combining facemask (FM) and maxillary skeletal expander (MSE)", Seminars in Orthodontics, vol. 24, issue 1, pp. 95-107, (2018).
International Search Report and Written Opinion dated Jul. 30, 2019 for PCT application No. PCT/US2019/21707.
International Search Report and Written Opinion dated Nov. 29, 2019 for PCT application No. PCT/US2019/041667.
16 Pages, Jan. 23, 2019, U.S. Appl. No. 16/115,564, US.
4 Pages, Mar. 11, 2019, U.S. Appl. No. 16/115,564, US.
13 Pages, Jul. 17, 2019, U.S. Appl. No. 16/115,564, US.
10 Pages, Sep. 9, 2019, U.S. Appl. No. 16/115,564, US.
3 Pages, Jul. 1, 2020, 18822553.6, EP.
7 Pages, Mar. 15, 2021, U.S. Appl. No. 16/630,818, US.
9 Pages, Nov. 4, 2021, U.S. Appl. No. 16/630,818, US.
6 Pages, Feb. 16, 2022, 18822553.6, EP.
8 Pages, May 24, 2022, U.S. Appl. No. 16/978,746, US.
Application No. 201980059222.1, dated Dec. 27, 2021, CN, 7 Pages.
Extended European Search Report dated Mar. 21, 2022 for EP application No. EP19833137.3.
15 Pages, May 31, 2021, 201880087707.7, CN.
4 Pages, Mar. 15, 2023, 18822553.6, EP.
8 Pages, Jan. 10, 2023, 2020-546298, JP.
7 Pages, Sep. 7, 2023, U.S. Appl. No. 17/259,432, U.S.

* cited by examiner

THE GUIDE MAINTAINS THE 1mm SEPARATION DISTANCE BETWEEN THE PALATE AND THE ANCHOR BODIES

MAXILLARY EXPANDER AND PROTRACTION DEVICE

CONTINUITY INFORMATION

This application is related to and claims priority to U.S. Provisional Application filed Jun. 15, 2018 with Ser. No. 62/685,801 and with confirmation number 5437, U.S. Provisional Application filed Nov. 24, 2017 with Ser. No. 62/590,363 and with confirmation number 3619, U.S. Provisional Application filed May 26, 2018 with Ser. No. 62/676,969 and with confirmation number 1055, U.S. Provisional Application filed Jul. 17, 2018 with Ser. No. 62/699,264 and with confirmation number 7667, and U.S. Patent Application filed Aug. 29, 2018 with Ser. No. 16/115,564 and with confirmation number 6177; all of which are incorporated herein by reference for all purposes.

BACKGROUND

Current maxillary skeletal anchorage expanders (hereafter in the background called "expander(s)") are devices that can be used to treat patients with transverse maxillary as well as anterior-posterior deficiency. With children, palatal expanders have been used to expand the maxillary arch to create room for the growth of permanent teeth or to widen the upper jaw so that the bottom and upper teeth will fit together better. In some cases, the jaw is expanded as a treatment to a compromised airway. Some known palatal expanders comprise and expand the maxillary arch by tooth (molar) borne anchorage means (bands) bridged together by an adjustable screw mechanism (see U.S. Pat. No. 5,564,920 Klapper). As the screw is turned, a bilateral force is generated against the teeth and jaws to cause displacement of the teeth and the maxillary arch. Once installed, the adjustable screw is rotated using a tool. The screw conventionally comprises two opposing halves, each half having a threaded portion. The force from the expanding screw is transferred through arms of the device to the banded molars and ultimately results in expansion of the maxillary dental arch and/or growth from the median palatine suture. The expander is left in for a therapeutically effective period and the patient, or patient's caregiver, activates the expander by rotating the screw a predetermined amount over a predetermined period appropriate to the expander screw configuration, age of the patient, and condition for which treatment is applied (e.g., a ¼ turn producing 0.25 mm of movement once per week; a ¼-½ turn a day producing 0.25-0.50 mm of movement a day, etc.). Following a desired expansion, a holding phase is performed, leaving the expander in place for 3-6 months for stabilization, during which time the screw is locked in place to prevent the screw from backing up. During the holding phase the tooth/jaw interface stabilizes in a new position and the palatine suture grows back together across the space, after which time the expander is removed. The expander described above expands the space across the palatine suture via forces that are directly applied to only the teeth.

Another known expander device is demonstrated in U.S. Pat. No. 9,351,810 (Moon). The Moon expander uses four mini screws/temporary anchorage devices to mount a pair of bodies to the ceiling of the hard palate on either side of palatine suture. Each of the bodies in Moon also comprise a pair of extending arms and a pair of tooth anchorage bands devices similar to that used by Klapper as mentioned above. The Moon expander comprises a double ended screw located between the pair of bodies. When the double ended screw in Moon is rotated, forces are applied directly not only to the teeth, but also by the mini screws to the hard palate on either side of the palatine suture. Unlike the Klapper device, since force is also applied directly to the hard palate, a reduced amount of force can be applied to the teeth, and a greater amount of force on the bone, which reduced force means stresses on the tooth/jaw interface can be reduced. However, the Moon expander also has a number of disadvantages. By applying forces directly to the hard palate, the mini screws are put under stress and thus are subject to potential breakage, as is also the bone structure in the area where the screws are inserted. Further, although Moon applies less force to the teeth, it nevertheless transmits force to and causes movement of the teeth, which may not be desired. For example, when treating transverse maxillary deficiency in skeletally mature individuals, transmitting force to the teeth can result in undesired alveolar effects, such as alveolar "bending," tooth root resorption, and potentially even a "scissors bite." Furthermore, Moon's expander is only supported by two mini implants on each side of the median palatine suture, which often times in more skeletally mature individuals is insufficient and inefficient at generating the desired orthopedic effects, such that could occur with surgical osteotomy followed by expansion. In these skeletally mature cases, the limit of only two mini implants on each side of the median palatine suture (4 in total) not only is inefficient at generating a desired orthopedic expansion, but also results in increased stresses on each individual mini implant and the bone around those implants. This is evidenced by the fact Moon's expander often time requires full activation of the expansion screw in skeletally mature individuals, which is 8-12 mm of activation, just to achieve opening of the median palatine suture and achieve 1-2 mm of orthopedic expansion. As a consequence of this inefficient skeletal expansion and as a consequence of the design lacking the ability to interchangeably attach different size expansion screws to the anchor bodies, in many cases when treating mature individuals, at least two of Moon's devices are required to achieve satisfactory skeletal expansion. Requiring multiple uninstallations and installations of the device causes patients to be subjected to multiple surgical procedures, increased cost, and discomfort, and requires greater effort by the clinician. Also, while Moon's device can be used to apply protraction forces to patients with anterior-posterior maxillary deficiencies, the device's reliance on the teeth for stability necessitates that protractionary forces must be transmitted at least partially to the teeth instead of wholly to the bone structure.

One thing that is needed, therefore, is an expander that does not directly affect movement of teeth during expansion of the palatine suture, that enables the attachment of interchangeable expansion screws of different sizes, that reduces forces and stress applied to screws as well as the local bone supporting the screws and yet is able to more effectively distribute force along the median palatine suture, and that enables for true skeletal protraction. Stated in another way, what is needed is an expander that can generate more substantial and efficient orthopedic effects than the prior art, while at the same time eliminating alveolar and tooth effects, and, reducing discomfort and inconvenience for the patient and clinician. Maxillary deficiency can also occur in a forward (sagittal) direction. An orthodontic device known as the Keles Facemask includes both a palatal expander and an external worn orthodontic appliance such as a face bow that impart lateral and protraction forces via molar bands that are fixed to a patient's dentition. Jaw movement imparted by the Keles device causes forwardly directed downward growth of the maxilla. The Keles device relies on tooth borne forces that are then transferred to the maxilla, which is less than ideal, since movement that might otherwise be imparted to the maxilla bone is instead imparted to teeth.

Another device invented by De Clerck utilizes a bone anchor comprised of a Bollard miniplate to transfer forward protraction forces to the maxilla. The De Clerck device can be used for maxillary protraction, but it to causes rotation of the maxilla, which causes movement and growth of the maxilla to be directed not just forward, but downward, and as well requires relatively invasive mucosal surgery for installation.

What is needed is an orthodontic device that is able to impart forward movement and growth of the maxillary skeletal complex and the 9 bones that articulate with the maxilla in a manner that improves upon the prior art.

FIGURES

Figure 1B:
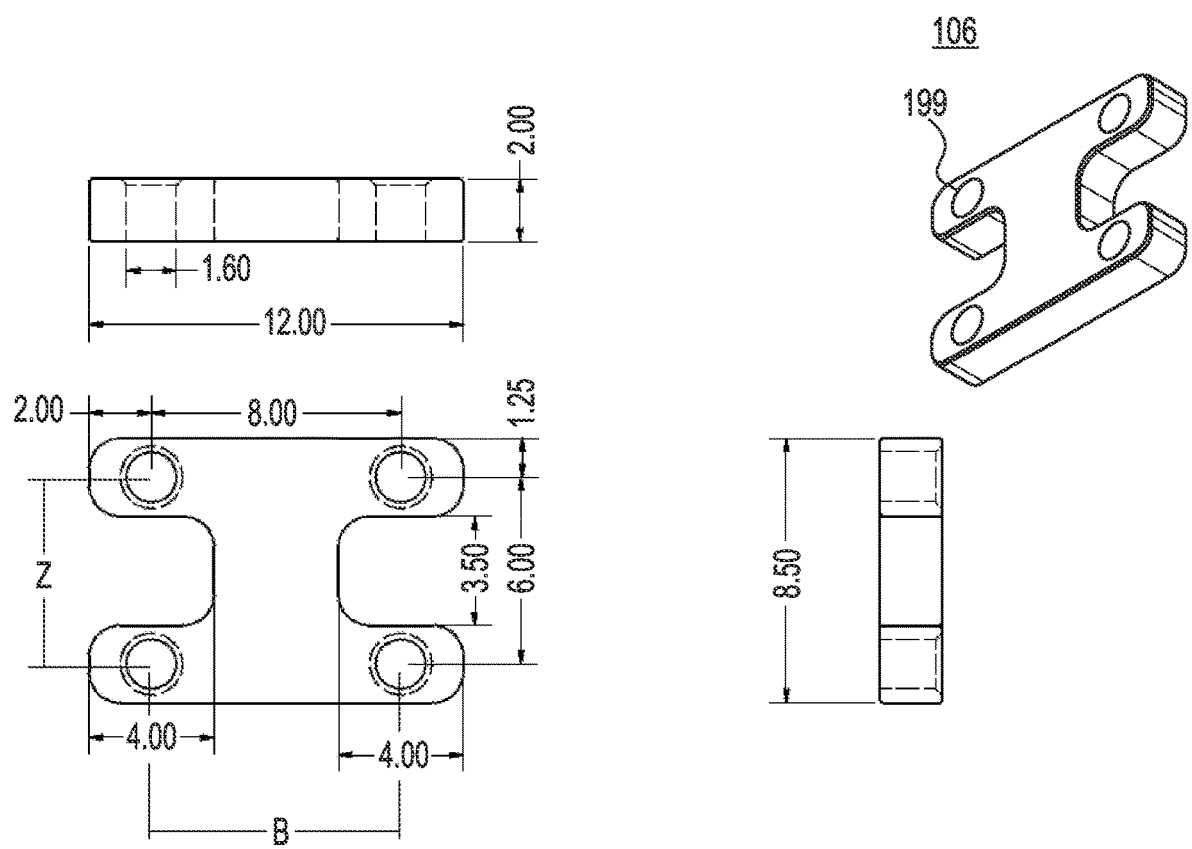
Figure 1C:
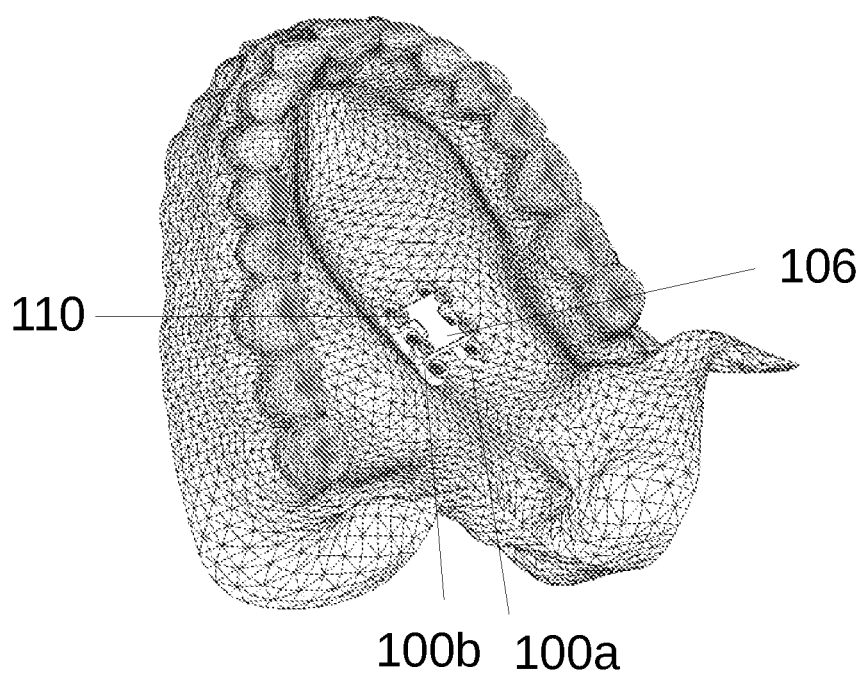

Referring to FIGS. 1a-c, there are seen representations of components of a skeletal anchorage device before being coupled intraorally to a patient's upper palate on either side of the median palatine suture.

Figure 2A:
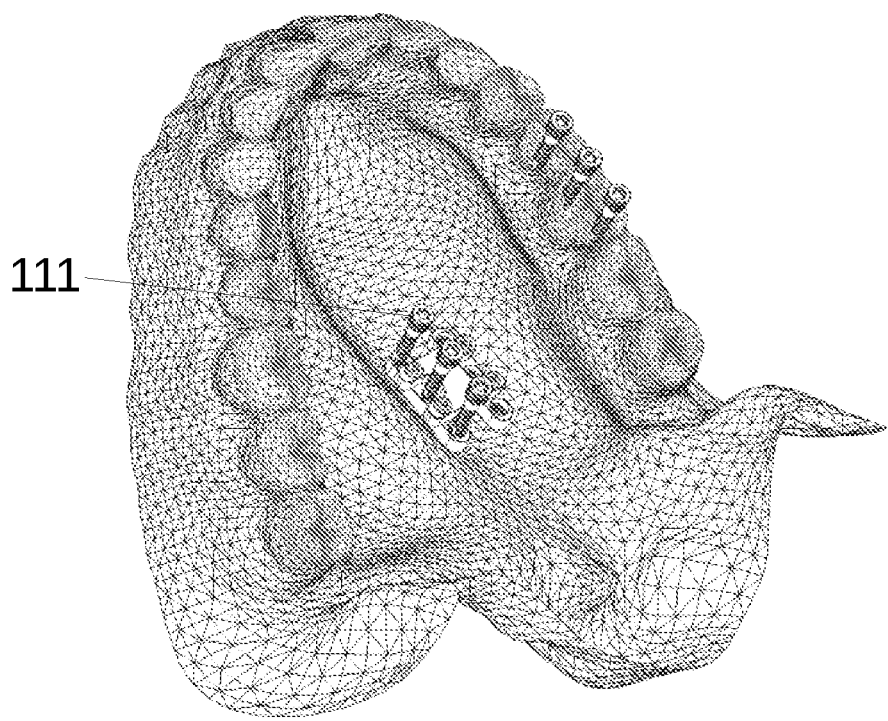
Figure 2B:
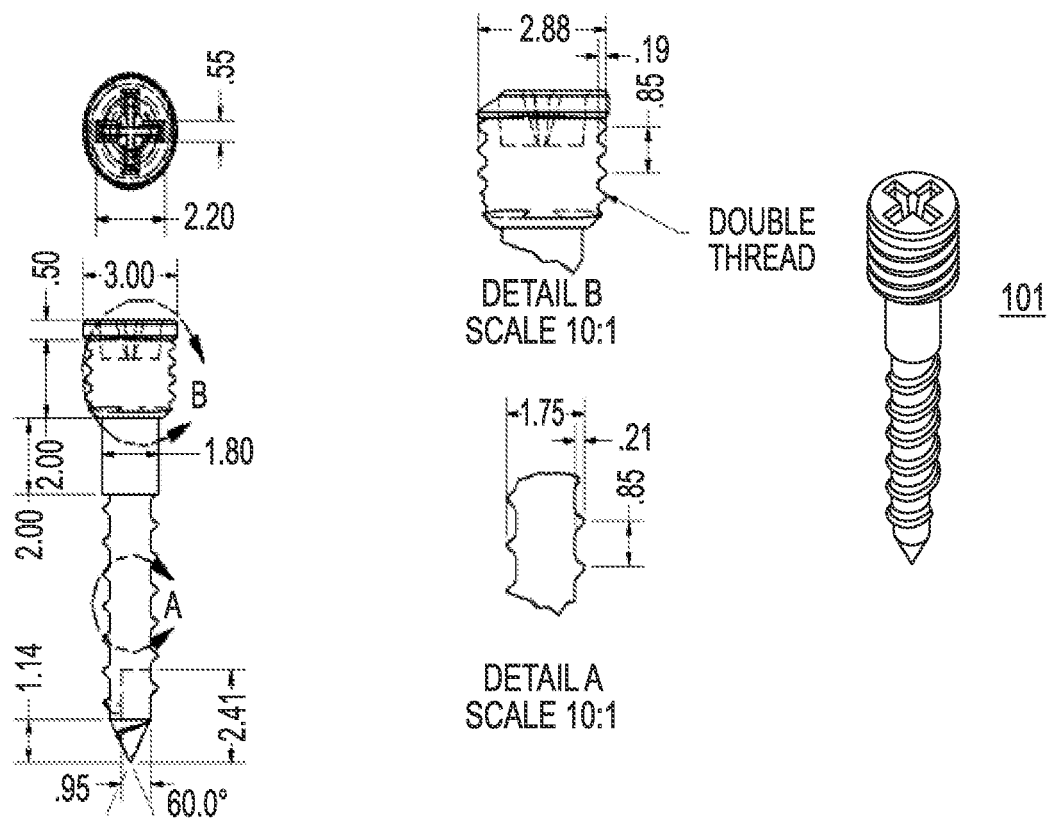

Referring to FIGS. 2a-b, there are seen representations of components of a skeletal anchorage expander device during their coupling to the hard palate on either side of the median palatine suture.

Figure 3:
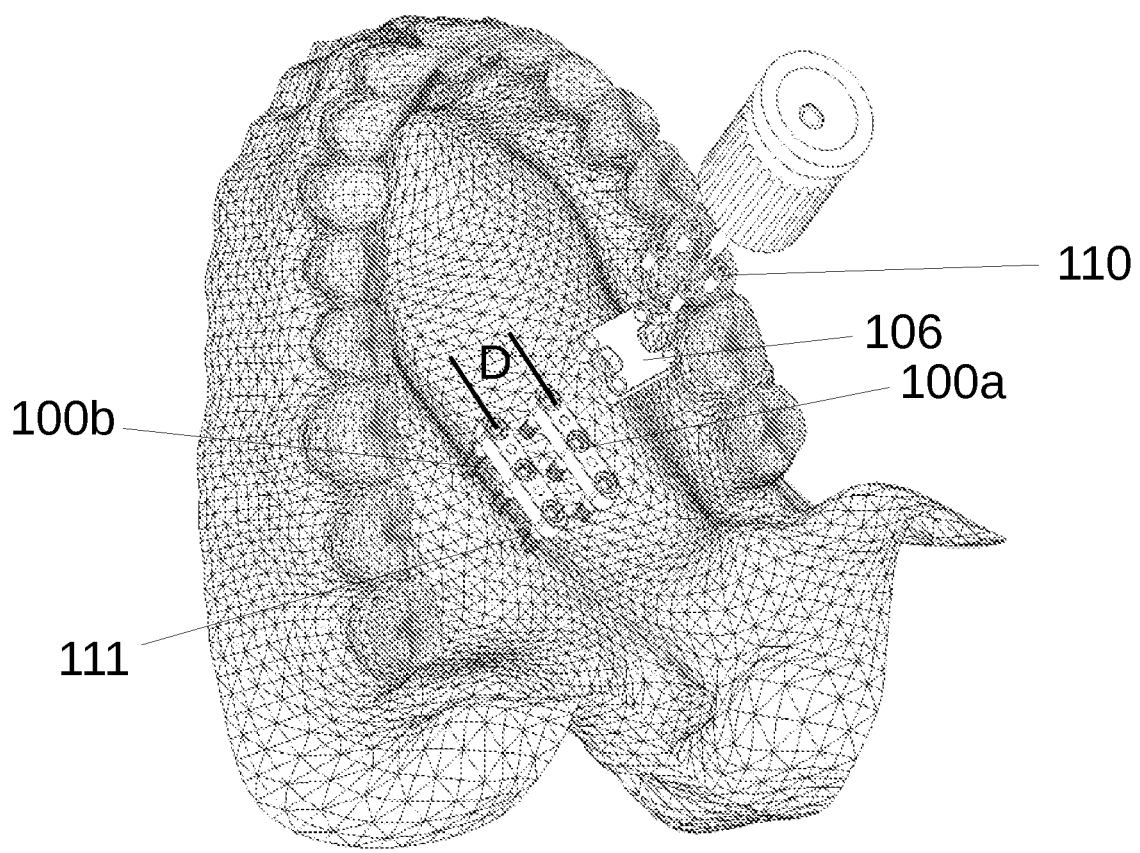

Referring to FIG. 3, there is seen a representation of components of a skeletal anchorage expander device after a pair of first bodies has been coupled to a palate of a patient and after a first fixed aligner is removed.

Referring now to FIGS. 4a-j, there are seen representations of components of a skeletal anchorage expander device that comprised of an adjustable aligner and/or a pair of first bodies.

Figure 5A:
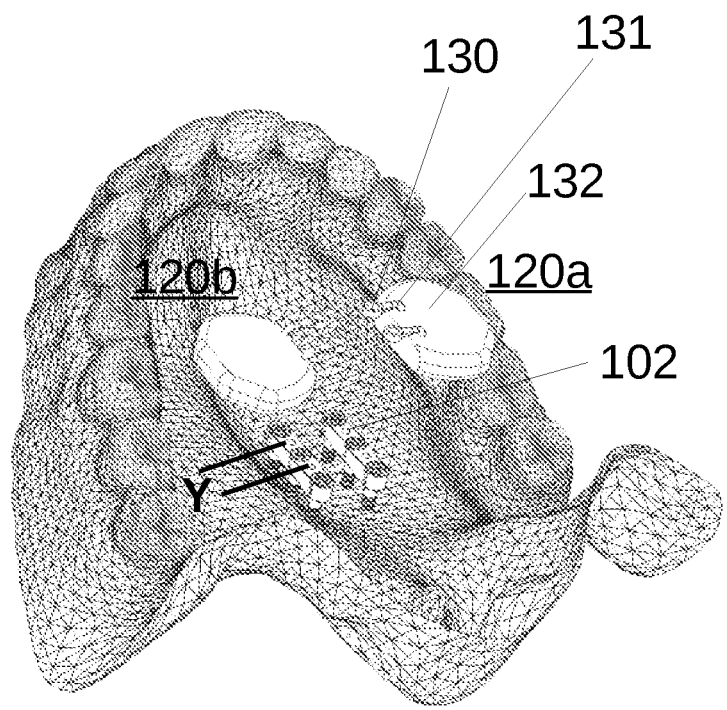
Figure 5B:
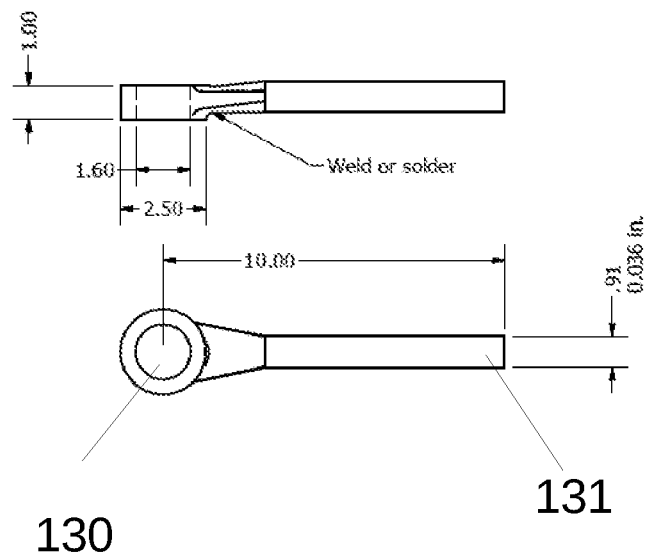

Referring to FIGS. 5a-b, there are seen representations of components a skeletal anchorage expander device, including of a pair of first bodies and a pair of appliances before the appliances are coupled to the pair of first bodies.

Referring to FIGS. 6a-d, there are seen representations of components of a skeletal anchorage expander device including a pair of appliances coupled to a pair of first bodies before and after an adjustable aligner is coupled to the pair of first bodies and the appliances.

Figure 7A:
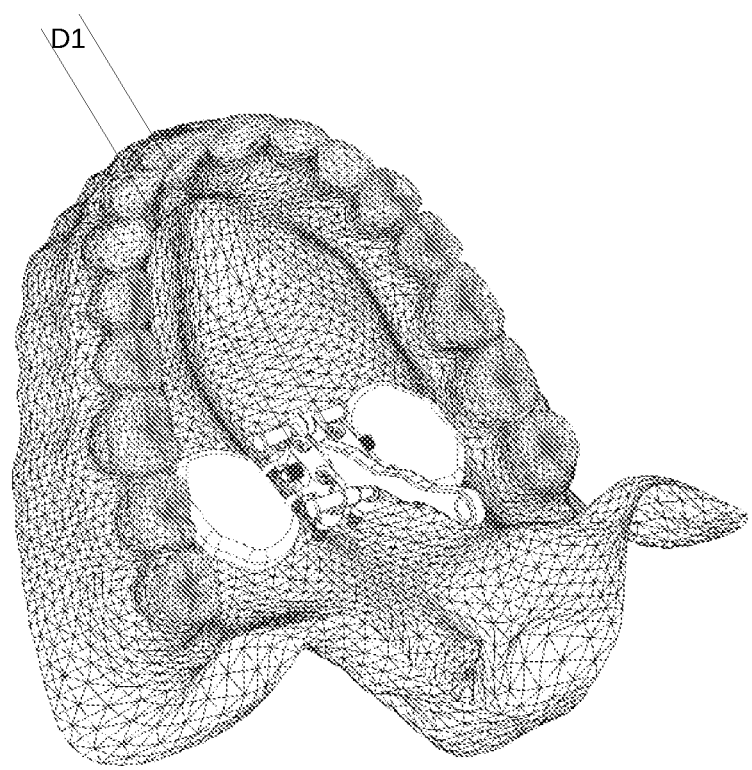
Figure 7B:
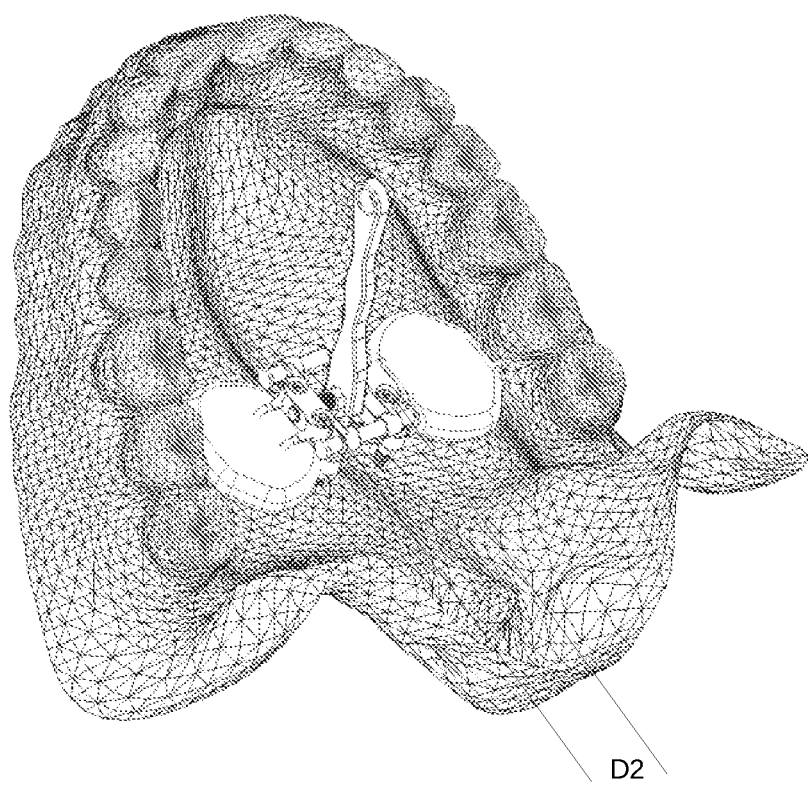

Referring to FIGS. 7a-b, there are seen representations of components of a skeletal anchorage expander device comprised of appliances before and after a distance between an adjustable aligner is increased by an adjustment mechanism.

Figure 8:
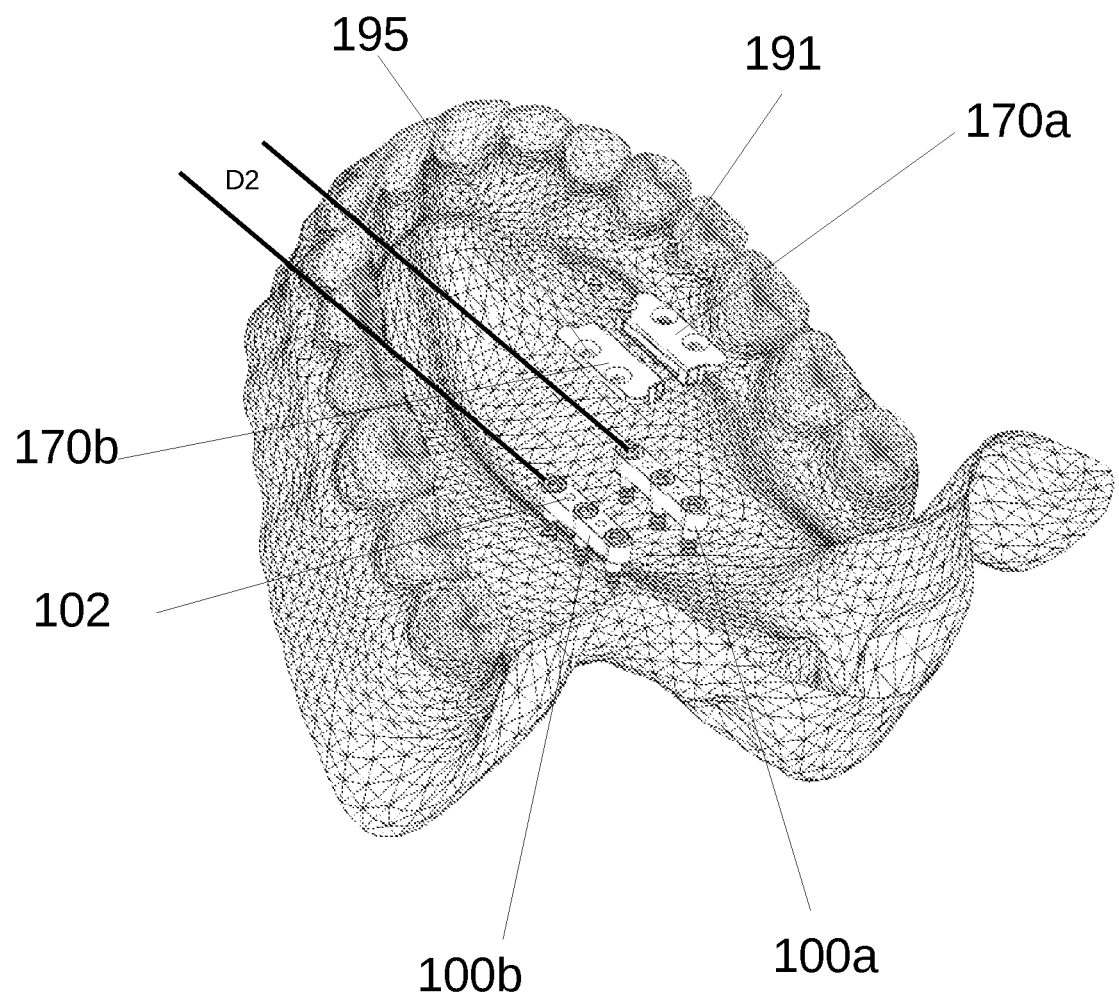

Referring to FIG. 8, there is seen a representation of a pair of first bodies after a distance between the adjustable aligner is increased by a clinically desired amount the adjustable aligner and appliances are removed.

Figure 9:
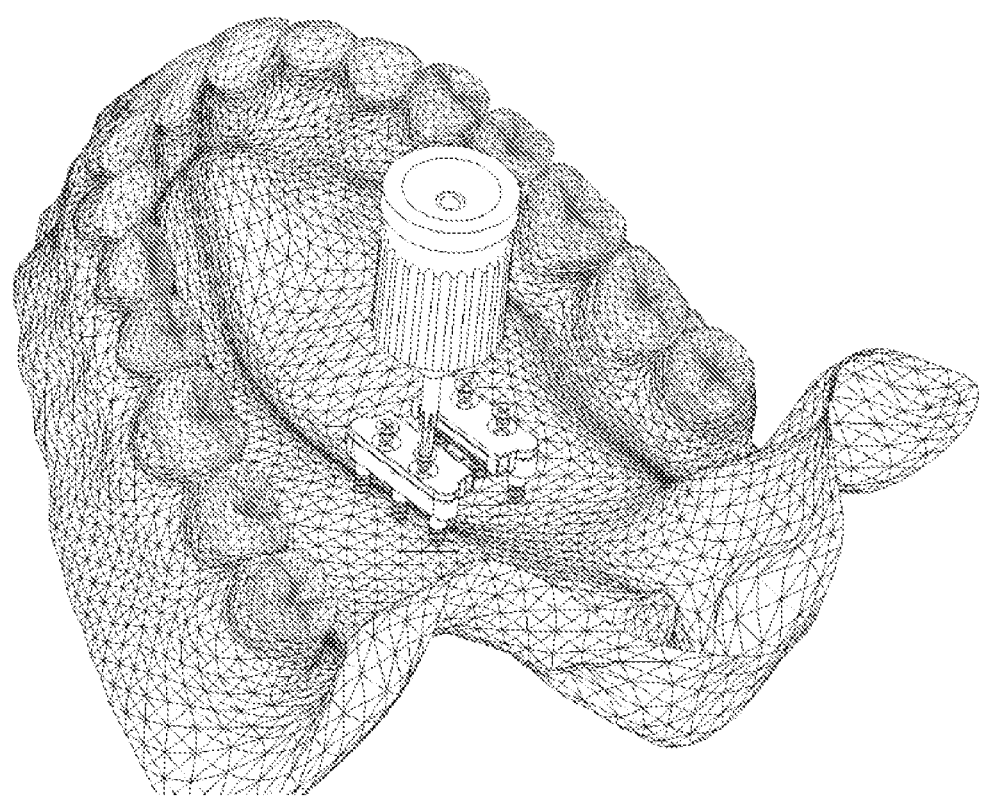
Figure 10A:
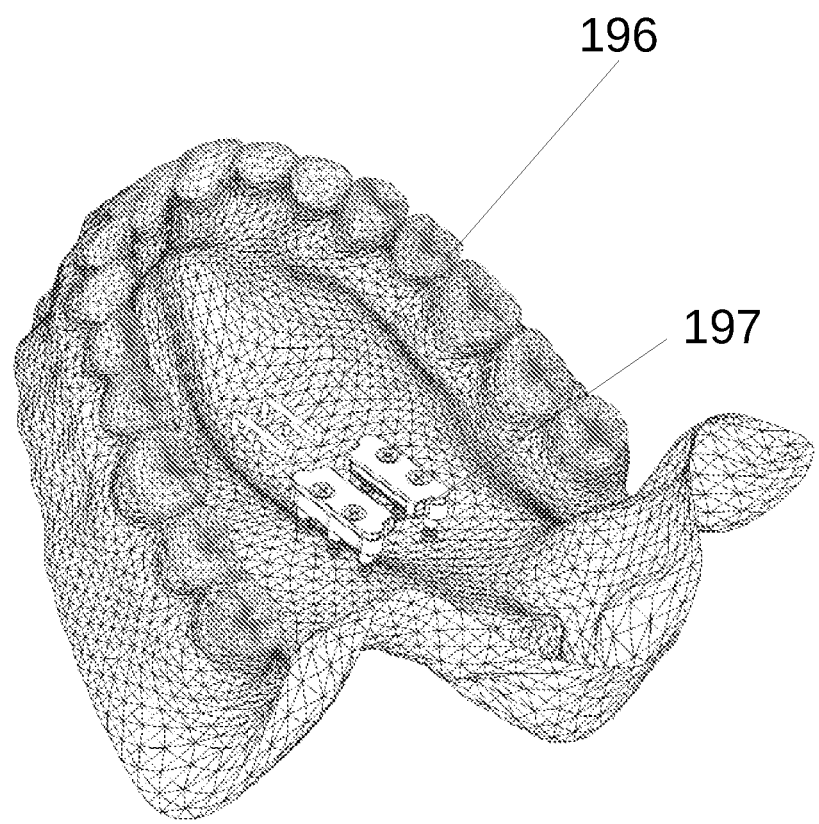
Figure 10B:
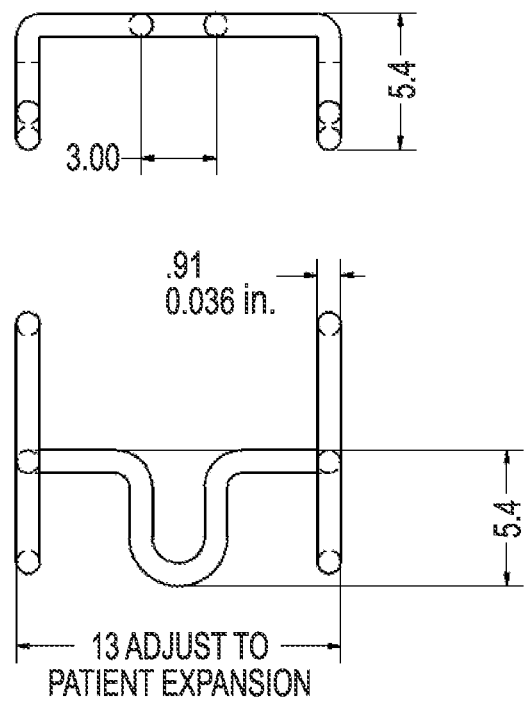
Figure 10B:
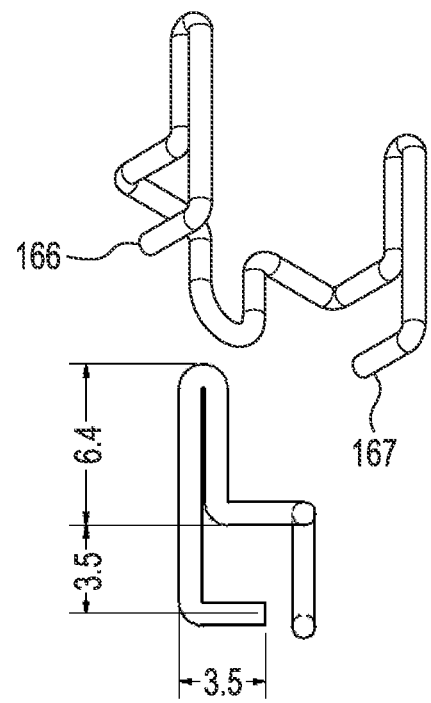
Figure 10C:
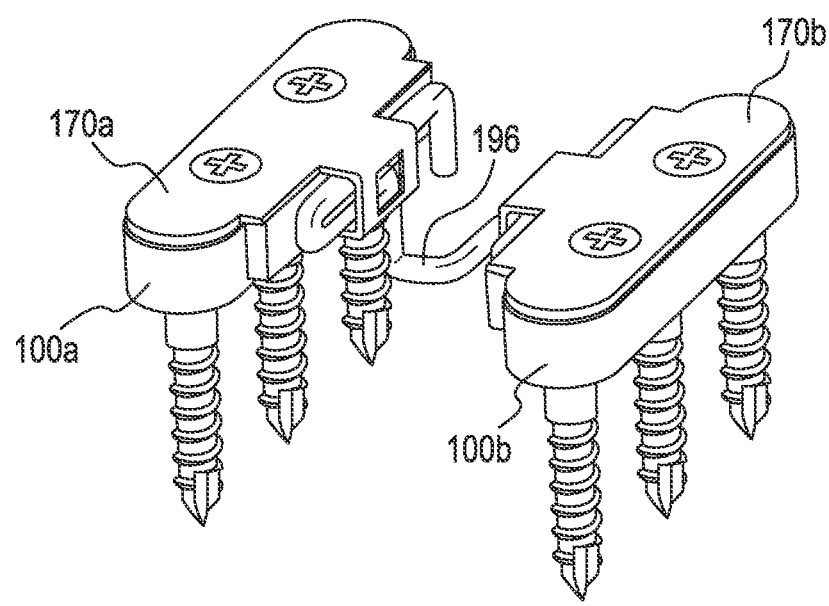
Figure 10D:
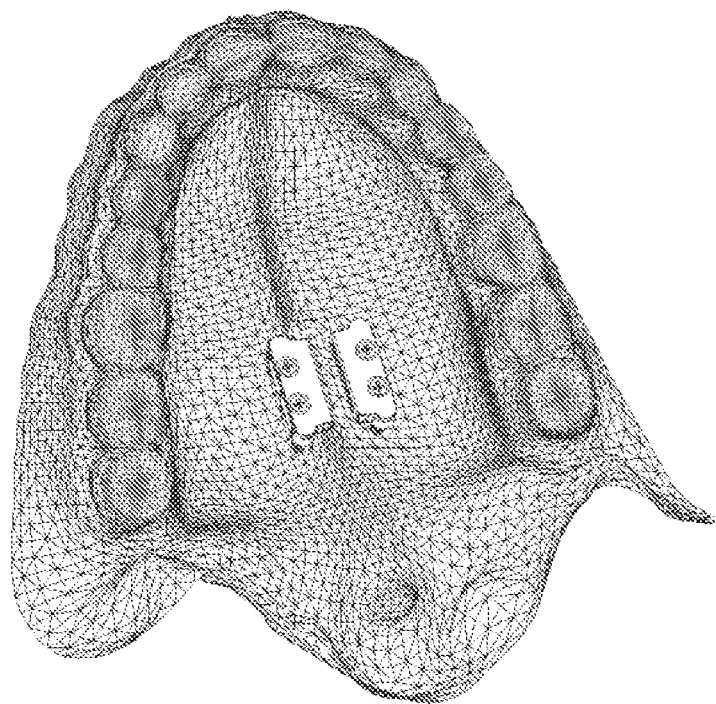

Referring to FIG. 9, there is seen a representation of a pair of first bodies and a pair of third bodies after the pair third bodies are coupled to the pair of first bodies via respective fifth fasteners.

Referring to FIGS. 10a-d, there are seen representations of components of a skeletal anchorage expander device, including a second fixed aligner.

Figure 11A:
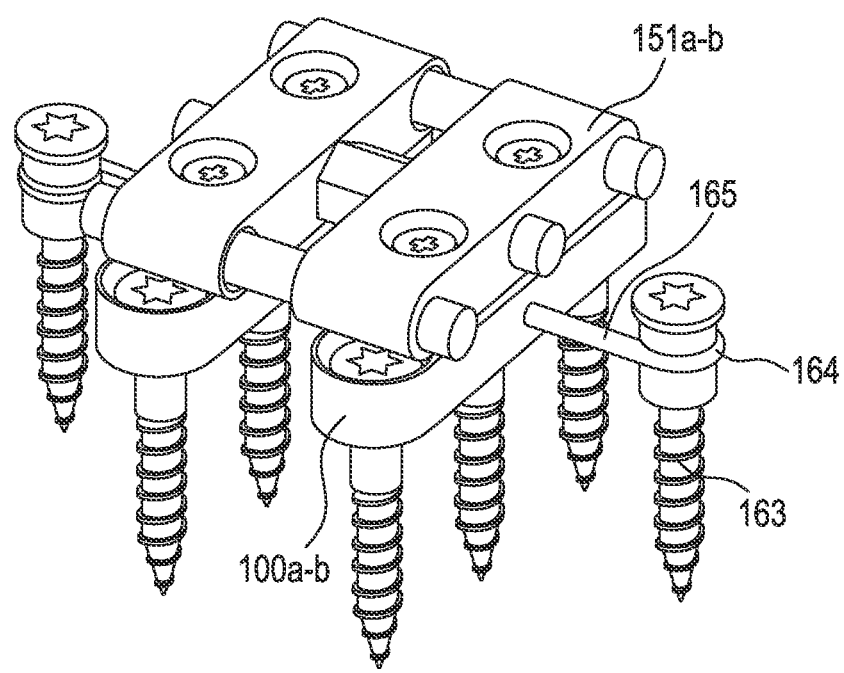
Figure 11B:
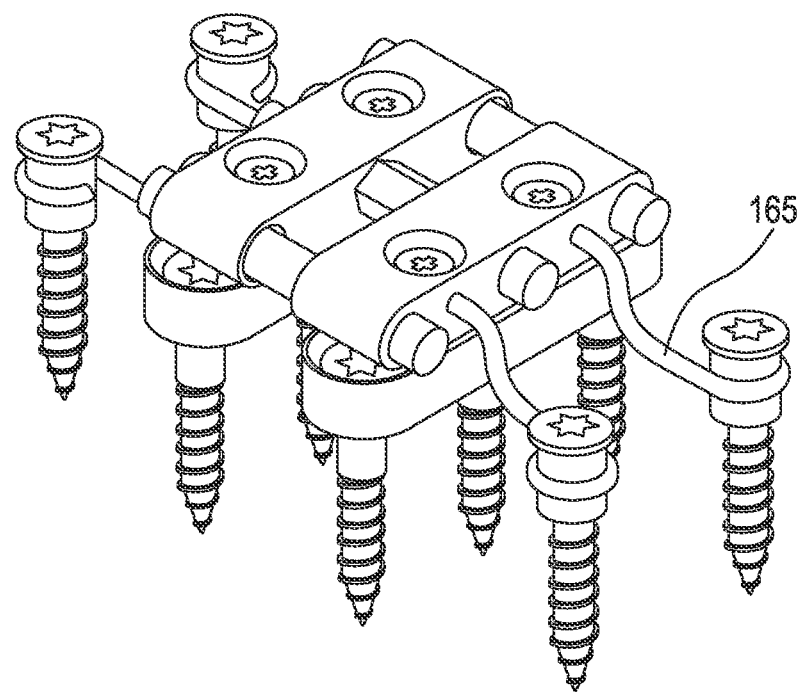

Referring to FIGS. 11a-b there are seen representations of a skeletal anchorage expander device comprised of additional bodies.

Figure 12A:
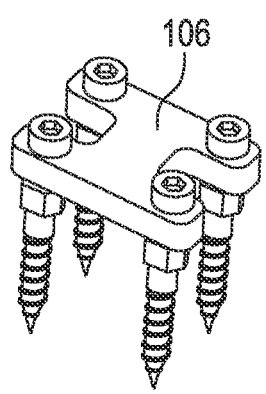
Figure 12B:
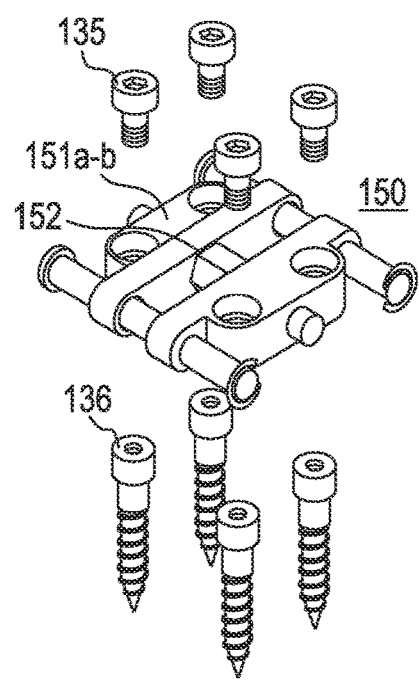
Figure 12C:
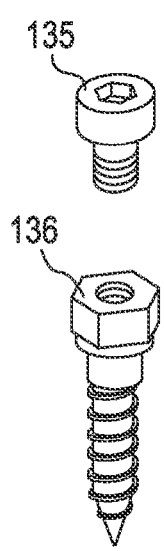

Referring to FIGS. 12a-c, there are seen representations of a skeletal anchorage expander device that does not necessarily rely on the use of a pair of first bodies.

Figure 13:
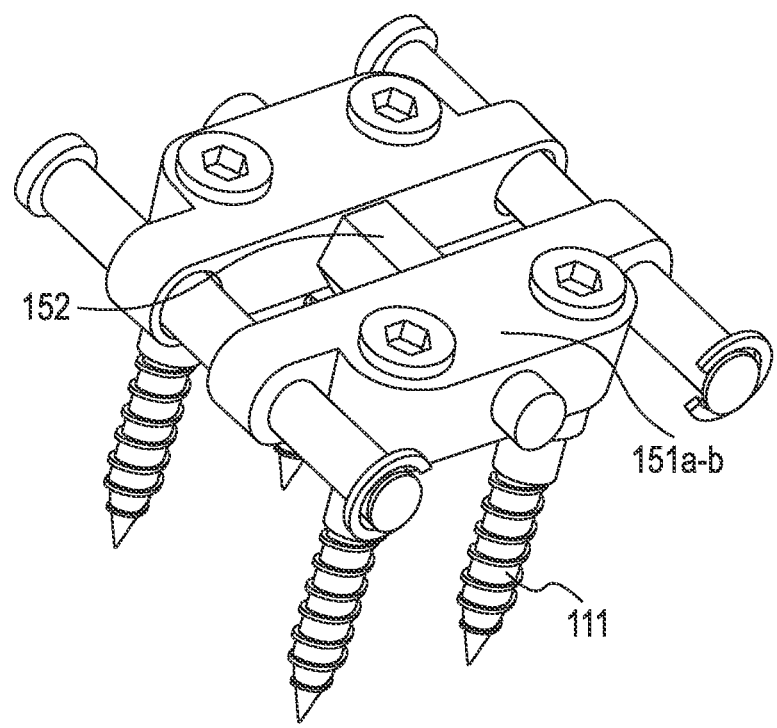

Referring to FIG. 13, there is seen a representation of another embodiment of a skeletal anchorage expander device that does not require use of first bodies 100a-b.

Figure 14:
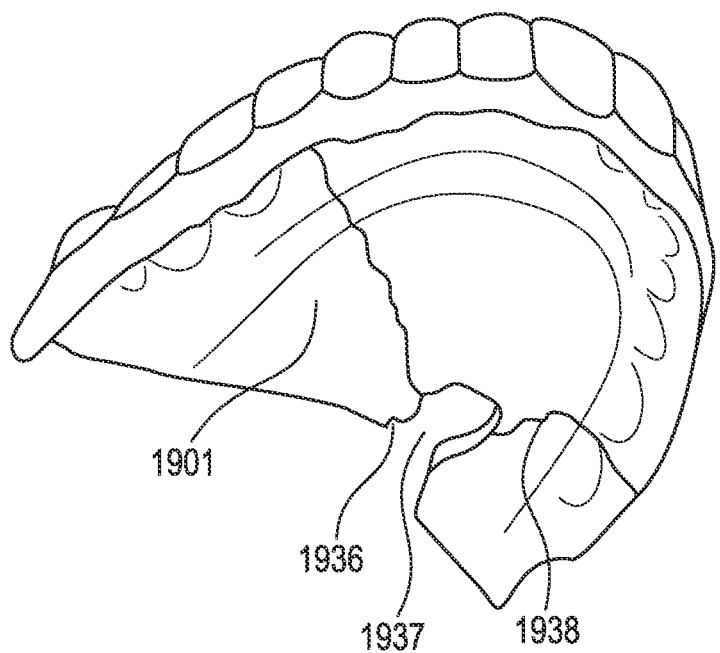

Referring to FIG. 14, there is seen a representation of a third fixed fastener.

Figure 15A:
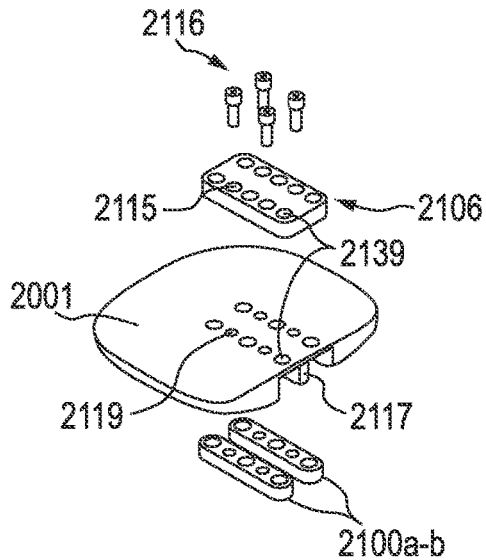
Figure 15B:
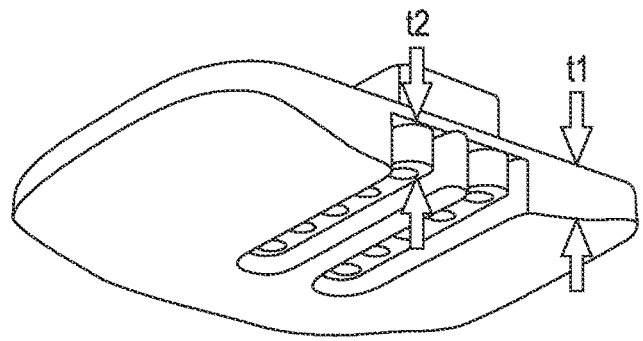
Figure 15C:
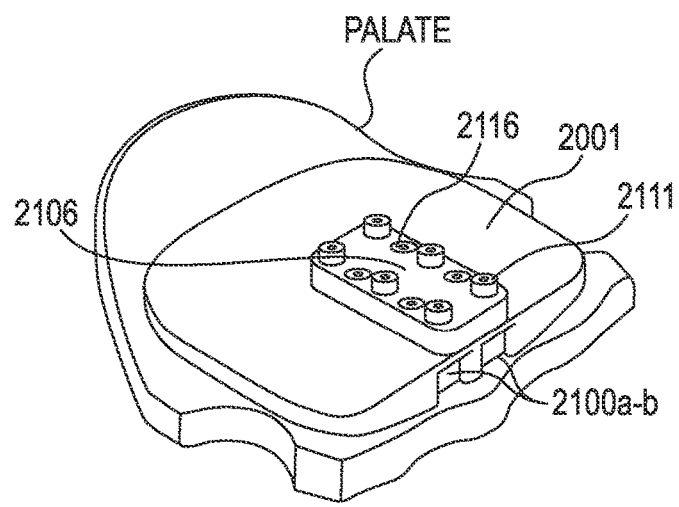

Referring to FIGS. 15a-c, there is seen a representation of another third fixed fastener.

Figure 16A:
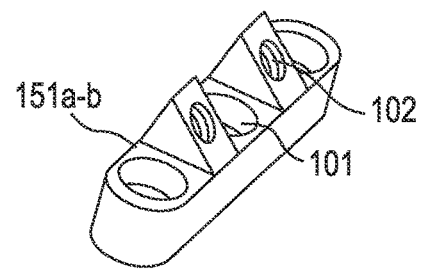
Figure 16B:
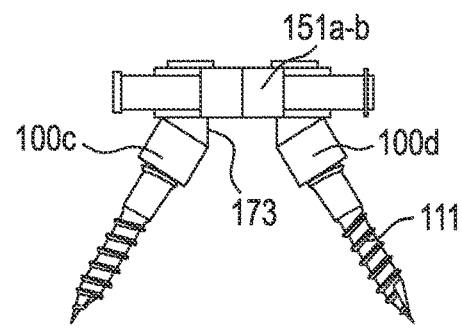
Figure 16C:
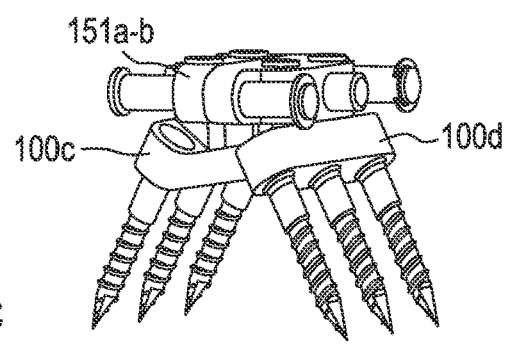
Figure 16D:
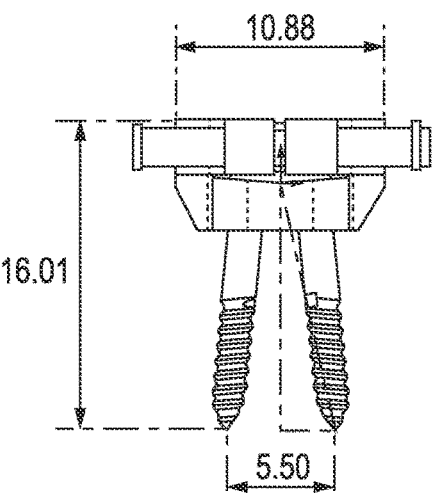

Referring to FIGS. 16a-c, there is seen another skeletal anchorage expander device.

Figure 17A:
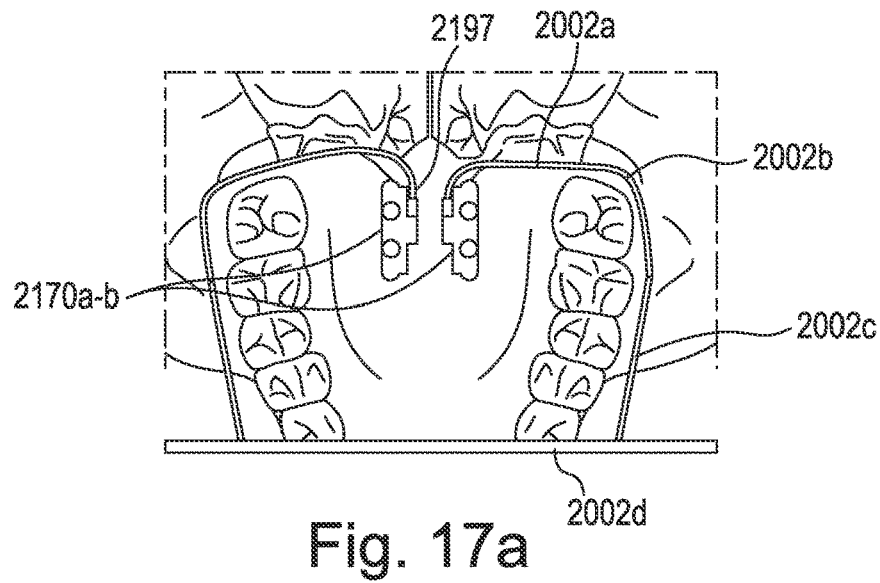
Figure 17B:
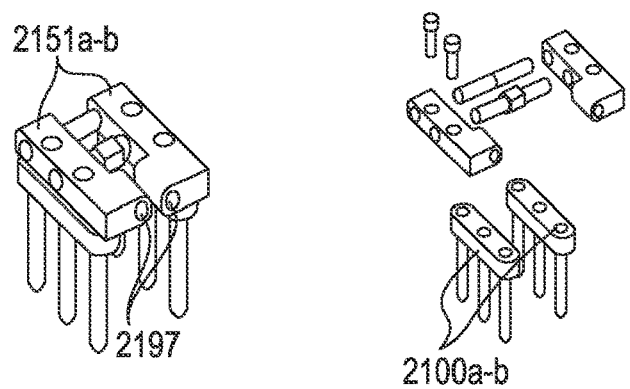
Figure 17C:
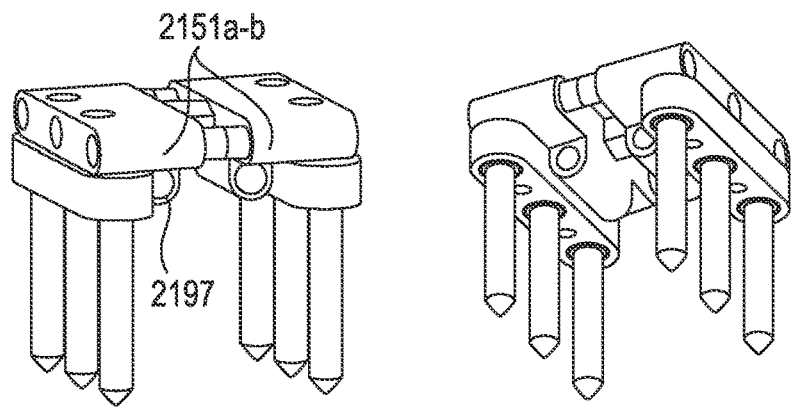

Referring to FIGS. 17a-c, there are seen representation of an orthodontic device comprised of a pair of third bodies and an externally worn orthodontic appliance coupled to the pair of third bodies.

Figure 18:
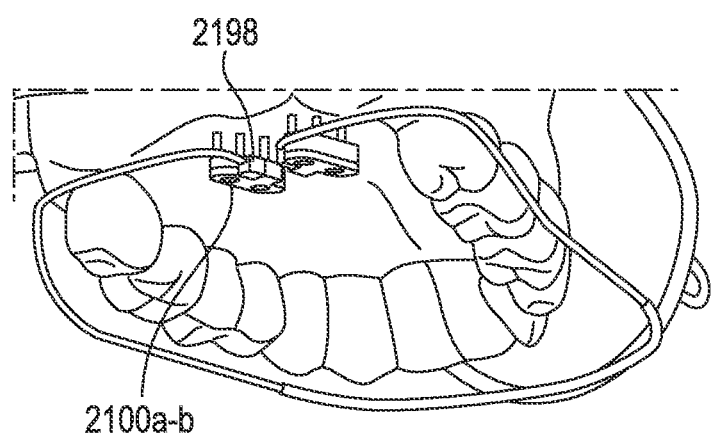

Referring to FIG. 18, there is seen a representation of a pair of first bodies coupled to an externally worn orthodontic appliance.

Figure 19A:
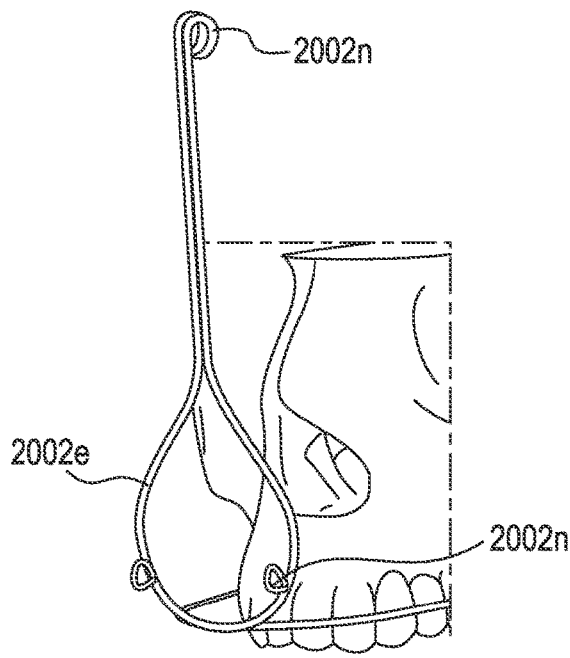
Figure 19B:
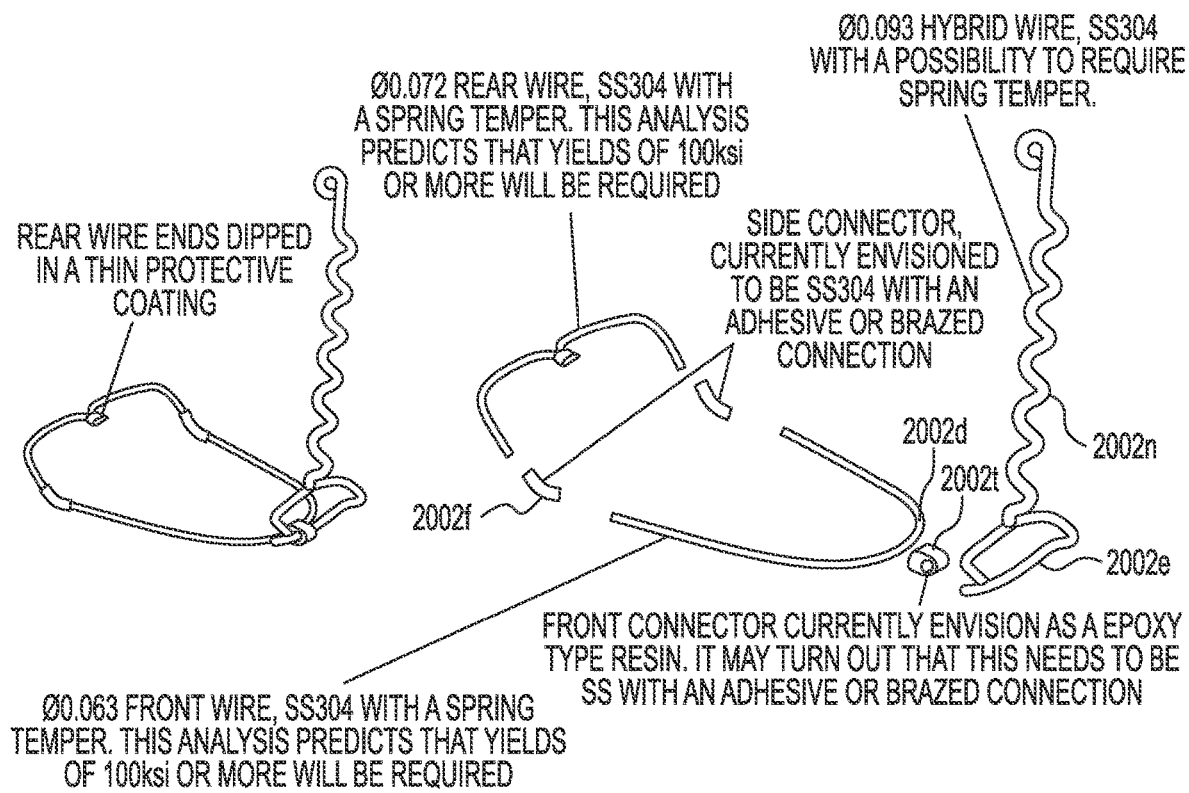

Referring to FIGS. 19a-b, there are seen other representations of an externally worn orthodontic appliance.

Figure 20A:
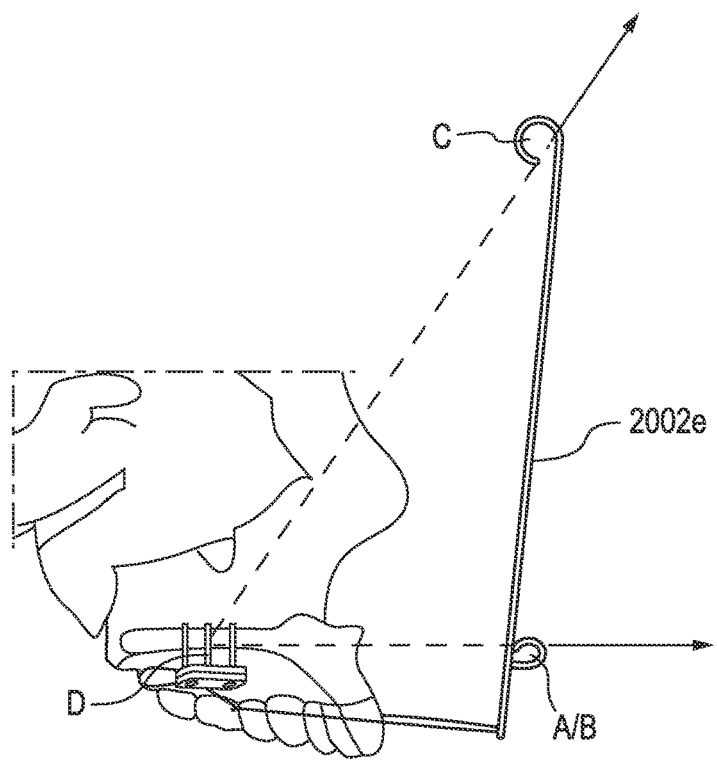
Figure 20B:
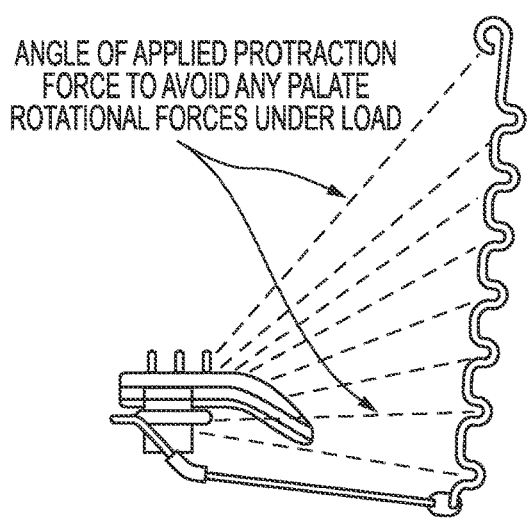
Figure 20B:
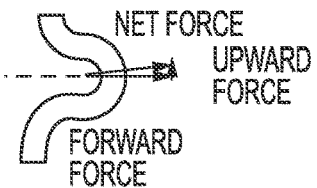

Referring to FIGS. 20a-b, there is seen a representation of external forces applied to an externally worn orthodontic appliance.

Figure 21A:
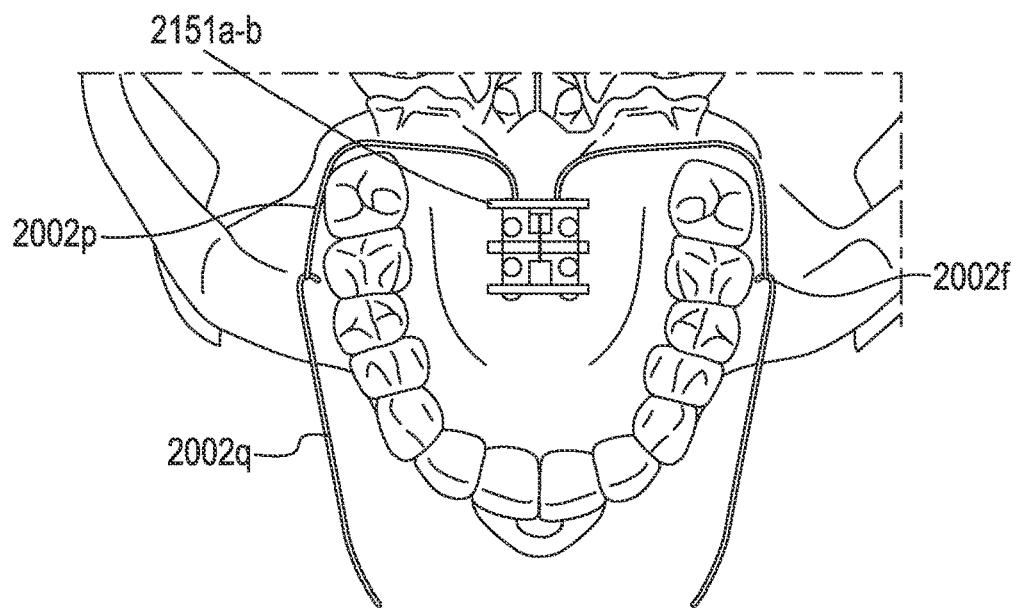
Figure 21B:
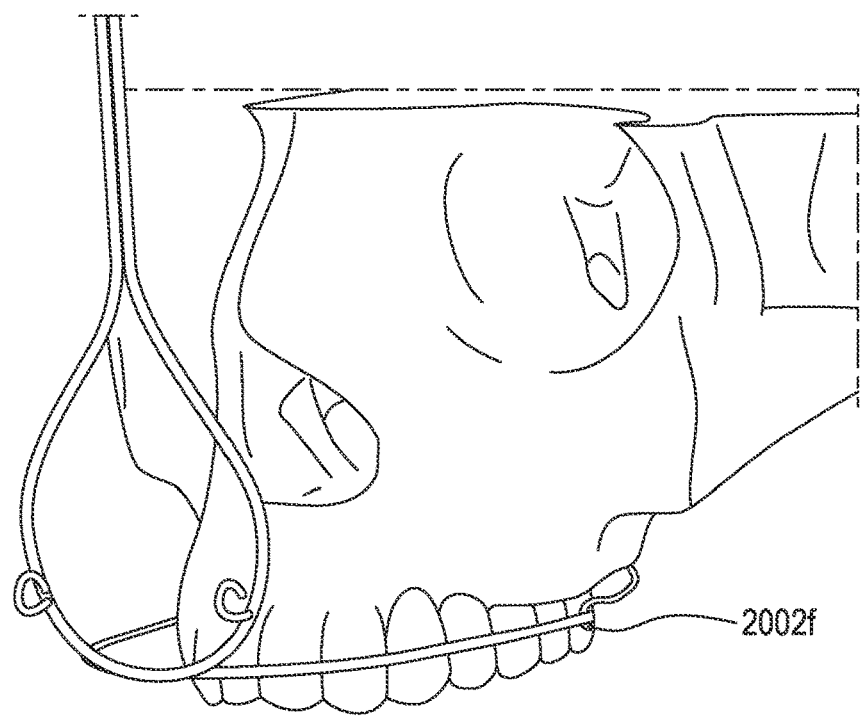

Referring to FIGS. 21a-b, there is seen another representation of an externally worn orthodontic appliance and its use.

SUMMARY

In one embodiment the present invention is directed to a medical device, comprising: at least two bodies, wherein each of the at least two bodies are configured to be coupled to a maxilla of a patient and/or to an appliance that is at least in part extra-oral, and wherein the at least two bodies are configured to apply forces to the maxilla without any coupling of the device to the teeth of a patient. In one embodiment the present invention further comprises an adjustment mechanism configured to variably maintain a distance between the at least two bodies. In one embodiment the present invention comprises couplers configured to couple to ends of the appliance. In one embodiment the present invention comprises the appliance. In one embodiment the present invention the adjustment mechanism comprises threads. In one embodiment with the at least two bodies coupled to the hard palate, the adjustment mechanism is configured to cause lateral movement of the hard palate. In one embodiment with the at least two bodies coupled to the maxilla, an extra-oral force applied to the orthodontic appliance causes forward or a combination of forward and upward movement of the maxilla. In one embodiment with the at least two bodies coupled to the hard palate, an extra-oral protraction force applied to the appliance causes forward or a combination of forward and upward movement of the maxilla. In one embodiment the external protraction force is applied to the appliance in a direction that is in-line to the at least two bodies. In one embodiment the at least two bodies are configured to be releasably coupled to the orthodontic appliance by a fastener. In one embodiment the fastener is configured to form an interference fit, snap fit, and/or a slip fit. In one embodiment the appliance comprises an intra-oral portion and an extra-oral portion, where the intra-oral portion and the extra-oral portion are releasably coupled. In one embodiment the at least two bodies are coupled by an adjustment mechanism configured to impart lateral movement to the maxilla. In one embodiment the adjustment mechanism comprises a body with two ends that have threads at only one end. In one embodiment a first of the at least two bodies comprise at a first aperture and a second aperture, each aperture disposed along a respective longitudinal axis, wherein the axis of the first aperture is not parallel to the axis of the second aperture. In one embodiment each of the at least two bodies comprise a plurality or threaded apertures configured to receive a threaded fastener. In one embodiment the device comprises the threaded fasteners, wherein each of the threaded fasteners comprise two sets of thread, wherein one of the two sets of threads is configured to mate with a respective threaded aperture of one of the at least two bodies, and wherein a second of the two sets of threads is configured to be threadably inserted into a maxilla. In one embodiment the maxilla is the hard palate. In one embodiment each body of the at least two bodies comprises a plurality of channels each configured to receive a fastener along a longitudinal axis, wherein the longitudinal axis of at least one channel of the plurality of channels is disposed in a non-parallel relationship to a longitudinal axis of at least a second channel of the plurality of channels. In one embodiment the longitudinal axis of the at least one channel is disposed in an angular relationship with respect to the longitudinal axis of the at least a second channel that is between 1 and 60 degrees.

In one embodiment, the present invention includes a maxillary expander, comprising: a pair of bodies comprised of a first body and a second body, wherein each of the pair of bodies is configured to be fixed intraorally to a palate of a patient; and a fixed aligner, wherein the fixed aligner is configured to be fastened to the pair of bodies to position the pair of bodies a predetermined distance apart. In one embodiment the present invention comprises a plurality of fasteners; a plurality of apertures formed in the pair of bodies; and a plurality of matching apertures formed in the fixed aligner; the plurality of fasteners configured to fasten the fixed aligner to the pair of bodies via insertion in the plurality of apertures in the pair of bodies and the fixed aligner. In one embodiment the present invention comprises the plurality of apertures comprise four apertures formed in the fixed aligner and two apertures formed in each of the pair of bodies. In one embodiment the present invention comprises a plurality of apertures formed in each of the pair of bodies; and a plurality of fasteners configured to fasten each of the pair of bodies body to the hard palate via insertion of the plurality of fasteners within the plurality of apertures. In one embodiment the plurality of apertures in each of the pair of bodies comprises at least three apertures. In one embodiment the fixed aligner comprises two ends, and wherein each of the pair of bodies is configured to be coupled to a respective one of the two ends. In one embodiment the fixed aligner is comprised of a wire. In one embodiment the fixed aligner consists of a single material. In one embodiment the expander is configured to be fixed to the palate with a space present between the pair of bodies and the tissue covering the palate.

In one embodiment the present invention includes a maxillary expander comprising: a first pair of bodies, wherein each of the bodies is configured to be coupled to a palate of a patient; and an adjustable aligner, wherein the adjustable aligner is configured to be releasably fastened to the pair of first bodies to vary a first distance between the first pair of bodies by applying an expansionary force to the first pair of bodies. In one embodiment the adjustable aligner comprises a second pair of bodies and an expansion screw disposed between the second pair of bodies. In one embodiment the present invention comprises a pair of appliances and at least two supports, wherein each support is comprised of a first end and a second end, wherein first ends of at least two of the supports are each coupled to and extend from a respective one of the first pair of bodies, and wherein second ends of the at least two of the supports are each coupled to an appliance. In one embodiment the adjustable aligner comprises a pair of appliances each coupled to a respective one of the second pair of bodies, wherein each of the appliances is configured to match a shape of the palate. In one embodiment the appliances comprises silicone or acrylic. In one embodiment the appliances are not configured to couple to any teeth of the patient. In one embodiment each of the first pair of bodies comprises three apertures configured to receive fasteners. In one embodiment the three apertures are threaded. In one embodiment each of the second pair of bodies is configured to be coupled to respective ones of the pair of first bodies by at least two screws.

In one embodiment the present invention includes a method of applying forces to an maxilla of a patient without engagement of any teeth of the patient, comprising the steps of: providing at least two bodies; coupling the at least two bodies to locations on the maxilla coupling an adjustable expander to the at least two bodies; and using the adjustable expander to apply a force to the at least two bodies to cause movement of the at least two bodies relative to one another and to cause expansion of the maxilla. In one embodiment the adjustable expander comprises threads at opposing ends of the expander. In one embodiment the movement of the at least two bodies is used to bilaterally expand the maxilla. In one embodiment the adjustable expander comprises threads at only one end of the expander. In one embodiment the movement of the at least two bodies is used to unilaterally expand the maxilla. In one embodiment the locations are on either side of the mid-palatine suture.

In one embodiment the present invention includes a maxillary expander comprising: at least one pair of bodies comprised of a first body and a second body, wherein, each body of the pair of bodies is configured to be coupled intraorally to a hard palate of a patient; and an aligner, wherein the aligner is coupled to the pair of bodies and configured to position the pair of bodies a distance apart to cause expansion of the palate without any engagement of the aligner or the at least one pair of bodies with any teeth of the patient. In one embodiment the aligner comprises a fixed aligner or an adjustable aligner. In one embodiment the at least one pair of bodies is selected from the group consisting of two appliances, two wires, and two fasteners. In one embodiment each body of the pair of bodies is configured to be coupled intraorally to the palate with at least one fastener. In one embodiment each fastener comprises two parts. In one embodiment the two parts comprises threaded portions and the two threaded portions are separated by a non-threaded portion. In one embodiment the two parts are separable. In one embodiment each of the at least one pair of bodies comprises apertures configured to receive fasteners having a body with threads at a top end and a bottom end, wherein the counter sunk apertures comprise threads configured to threadably mate with the threads at the top end. In one embodiment the apertures are countersunk. In one embodiment the threads at the top end and the threads at the bottom end are separated by a non-threaded portion.

In one embodiment the present invention is directed to a method of treating a maxillary deficiency, comprising the steps of: providing a pair of first bodies; coupling the pair of first bodies to a hard palate of a patient; attaching an externally worn appliance to the pair of first bodies; and applying a protraction force to the appliance to cause forward movement of the pair of first bodies. In one embodiment the method provides an expander between the pair of first bodies; and causing the expander to move to cause lateral movement the pair of first bodies relative to one another. In one embodiment the protraction force is aligned to cause only forward or forward and upward movement of the patient's maxilla. In one embodiment the protraction force generates little or no moments at the pair of first bodies. In one embodiment protraction force is applied in a direction that passes through the pair of first bodies and a point on the appliance where the force is applied to.

In one embodiment the present invention is directed to a method of laterally expanding a maxilla of a patient, comprising the steps of: intraorally attaching a pair of first bodies to the maxilla while maintaining a first space between the first bodies; attaching an adjustable aligner to the pair of first bodies; adjusting the adjustable aligner to cause an expansionary force to be applied to the pair of first bodies such that the first space is changed to a second space change; removing the adjustable aligner from the pair of first bodies; and affixing a first fixed aligner to the pair of first bodies to maintain the second space between the first bodies. In one embodiment the step of creating a first space between the bodies comprises affixing a second first fixed aligner to the pair of first bodies to create the first space; and subsequently removing the first fixed aligner from the pair of first bodies before attaching the adjustable aligner. In one embodiment the method comprise a step of affixing an appliance to each of the bodies. In one embodiment the method comprises a step of coupling the appliance to a hard palate and not to any of the teeth of the patient. In one embodiment each of the pair of first bodies is affixed to the palate on either side of the median palatine suture. In one embodiment the step of intraorally attaching the bodies includes a step of inserting at least three fasteners through each body and into the hard palate.

In one embodiment the present invention is directed to a method of expanding a median palatine suture, comprising the steps of: providing a pair of first bodies; providing a pair of acrylic appliances; intraorally coupling the pair of first bodies and the pair of acrylic appliances to a hard palate while maintaining a first distance between the pair of first bodies; and applying an expansionary force to the first bodies such to change the first distance between the first bodies to a second distance.

In one embodiment the present invention is directed to a method of expanding a maxilla, comprising the steps of: providing a pair of first bodies; coupling the pair of first bodies to a hard palate; attaching an aligner to the pair of first bodies; maintaining the pair of first bodies a distance below and apart from the hard palate. In one embodiment the aligner is an adjustable aligner. In one embodiment the aligner is a first fixed aligner. In one embodiment the distance is between 0.1 to 3 mm. In one embodiment the method comprises providing a spacer to between the pair of first bodies and the hard palate. In one embodiment coupling comprises use of threaded fasteners. In one embodiment the distance is maintained via locking of threads of the threaded fastener into the pair of first bodies.

In one embodiment, the present invention comprises a maxillary expander, comprising: at least two bodies, wherein each of the at least two bodies are configured to be coupled to a hard palate with a first distance between the at least two bodies and the palate; and an expander configured to maintain a second distance between the at least two bodies. In one embodiment the expander comprises ends that are threaded. In one embodiment the expander comprises only one end that is threaded. In one embodiment further comprises an aligner. In one embodiment the aligner comprises at least one body configured to be attached to the at least two of the bodies. In one embodiment, the aligner comprises a fixed aligner. In one embodiment aligner comprises an adjustable aligner. In one embodiment the aligner comprises the expander. In one embodiment the at least two bodies are configured to receive fasteners. In one embodiment the fasteners are configured to be received by at least one lateral support extending from each of the at least two bodies. In one embodiment the fasteners comprise screws. In one embodiment the fasteners comprise two threaded portions, wherein an outermost diameter of one or the two threaded portions is smaller than an outermost diameter of a second of the two threaded portions. In one embodiment the two threaded portions are separated by a non-threaded portion. In one embodiment the at least two bodies are disposed in a parallel relationship with respect to each other.

In one embodiment the present invention comprises a method of laterally expanding a maxilla, comprising the steps of: providing at least two bodies; coupling the at least two bodies to a hard palate; and attaching at least one aligner to the at least two bodies. In one embodiment the at least one aligner comprises a fixed aligner and/or an adjustable aligner. In one embodiment attaching the at least one aligner comprises attaching a fixed aligner and an adjustable aligner. In one embodiment the at least two bodies comprise fasteners. In one embodiment fasteners comprise threaded fasteners.

In one embodiment the present invention includes a medical device, comprising: at least two bodies configured to be coupled to a patient's maxilla, wherein each of the at least two bodies are configured to be coupled to an appliance that is at least in part extra-oral, wherein the appliance is configured to apply an extra-oral protraction force to the at least two bodies, and wherein the two bodies are configured to transfer the extra-oral force to the maxilla to cause movement and growth of the maxilla. In one embodiment the at least two bodies further comprising couplers configured to couple to ends of the orthodontic appliance. In one embodiment the device comprises the appliance. In one embodiment the appliance comprises an orthodontic face bow. In one embodiment an adjustment mechanism, wherein with the at least two bodies coupled to the maxilla, the adjustment mechanism is configured to transfer forces to the at least two bodies to cause the at least two bodies to apply forces to the maxilla and to cause lateral movement of the maxilla. In one embodiment with the at least two bodies coupled to the maxilla, an extra-oral force applied to the at least two bodies by the appliance causes forward or a combination of forward and upward movement of the maxilla. In one embodiment the external protraction force is applied to the appliance in a direction that that in-line to the at least two bodies. In one embodiment the at least two bodies are configured to be releasably coupled to the orthodontic appliance. In one embodiment the releasable coupling comprises an interference fit, snap fit, and/or a slip fit. In one embodiment the appliance comprises an intra-oral portion and an extra-oral portion, where the intra-oral portion and the extra-oral portion are releasably coupled. In one embodiment a first of the at least two bodies comprise at least a first aperture and a second aperture, each aperture disposed along a respective longitudinal axis, wherein the axis of the first aperture is not parallel to the axis of the second aperture. In one embodiment each of the at least two bodies comprise a plurality or threaded apertures configured to receive a threaded fastener. In one embodiment the device comprises the threaded fasteners, wherein each of the threaded fasteners comprise two sets of threads, wherein one of the two sets of threads is configured to mate with a respective threaded aperture of one of the at least two bodies, and wherein a second of the two sets of threads is configured to be threadably inserted into a maxilla. In one embodiment each body of the at least two bodies comprises a plurality of channels each configured to receive a fastener along a longitudinal axis, wherein the longitudinal axis of at least one channel of the plurality of channels is disposed in a non-parallel relationship to a longitudinal axis of at least a second channel of the plurality of channels. In one embodiment the longitudinal axis of the at least one channel is disposed in an angular relationship with respect to the longitudinal axis of the at least a second channel that is between 1 and 60 degrees.

The above should not limit the present invention as other advantages, benefits and embodiments are also within the scope of the invention as described in the detailed description below.

DETAILED DESCRIPTION

The figures referenced below refer to components and features of the present invention with reference indicators. Although same components may be shown in different figures, it should be noted that cumulative use of indicators with same components is not used when their use would be superfluous and/or make components more difficult to identify.

Referring to FIGS. 1a-c, there are seen representations of components of a skeletal anchorage device before being coupled intraorally to a patient's maxilla on either side of the median palatine suture.

In one embodiment, a skeletal anchorage device of the present invention comprises a pair of first bodies 100a-b (only one body shown in FIG. 1a) configured for intra-oral attachment to the maxilla along the upper palate on either side of the median palatine suture. In one embodiment, each body comprises a side configured to face the hard palate and an opposite top side. In one embodiment, one or both sides are flat. In other embodiments, the sides are parallel to each other. In one embodiment, at least a portion of one side is not parallel to the other side. In one embodiment, each of the first bodies 100a-b comprises a plurality of first apertures 101 and a plurality of second apertures 102 disposed along a longitudinal axis each first bodies. In one embodiment each first body comprises three first apertures 101 and two second apertures 102. In one embodiment, first apertures 101 extend through a thickness of the first bodies 100a-b. In one embodiment, second apertures 102 extend only a certain distance into the first bodies 100a-b and not all the way through. In one embodiment, the skeletal anchorage expander device also comprises a first fixed aligner 106 having a plurality of third apertures 199 configured to receive threaded first fasteners 110. In one embodiment, first fasteners 110 comprise screws configured to be received through the third apertures 199 and threadably screwed into the second apertures 102. In one embodiment, an equal number of third apertures 199 are formed on a lateral first left side of the first fixed aligner 106 as are formed on an opposite lateral right second side. In one embodiment, fixed aligner 106 comprises four third apertures 199. In one embodiment, fixed aligner 106 comprises a single integral body. In one embodiment, first fixed aligner 106 comprises a plate like structure. In one embodiment, the first fixed aligner 106 comprises an H-shaped geometry. In other embodiments, first fixed aligner comprises a geometry capable of having apertures formed at 4 corners. In one embodiment, third apertures 199 of the first fixed aligner 106 are configured with a longitudinal spacing "B" that enable them to be coupled to respective second apertures 102 of the pair of first bodies 100a-b with first fasteners 110 inserted in the apertures. In one embodiment, when the pair or first bodies 100a-b are coupled to the first fixed aligner 106 via fasteners, a lateral spacing of the third apertures 199 results in the pair of first bodies 100a-b being separated by a distance "Z". In one embodiment, first apertures 101 comprise a channel where the channel is counter sunk into first bodies 100a-b to a first depth that is less than a thickness of the first bodies and such that the channel is threaded along the first depth and configured to threadably receive threaded upper end of second fasteners 111 (FIGS. 2b-c) during screwable insertion of threaded bottom ends of the second fasteners into the palate. In one embodiment, first fixed aligner 106 and each first body 100a-b are dimensioned with the dimensions noted in FIGS. 1a and 1b.

In one embodiment of use (see FIG. 1c), a hard palate facing side of first fixed aligner 106 is positioned over respective bodies 100a-b, respective first fasteners 110 are inserted through the third apertures 199 of the first fixed aligner 106, and respective fasteners 110 are screwed into second apertures 102 to couple the first fixed aligner 106 to the pair of first bodies 100a-b. After first fixed aligner 106 and the pair of first bodies 100a-b are coupled, the combination is positioned over a hard palate of a patient such that one of first bodies 100a-b is positioned on one side of the median palatine suture of the patient and the other of first bodies 100a-b is positioned on the other side of the suture.

Referring to FIGS. 2a-b, there are seen representations of components of a skeletal anchorage expander device during their coupling to the hard palate on either side of the median palatine suture.

In one embodiment of use, after the first fixed aligner 106 and the pair of first bodies 100a-b are coupled to each other, they are positioned over the hard palate on either side of the median palatine suture and the combination is coupled to the hard palate via a plurality of threadable second fasteners 111. In one embodiment, each of the first bodies comprises a plurality of threaded first apertures 101 that extend between a hard palate facing side and an opposite side of the pair of first bodies. In one embodiment, each of the pair of first bodies 100a-b comprises three threaded first apertures 101. In one embodiment, threadable second fasteners 111 comprise a bottom portion configured to screw into the hard palate via a set of first threads and a top portion configured to screw into first apertures 101 via a second set of threads. In one embodiment, the first and second set of threads are separated by an unthreaded portion. In one embodiment the first set of threads are defied by an outer diameter that is smaller than an outer diameter of the second set of threads. In one embodiment, second fasteners 111 are dimensioned with the dimensions given in FIG. 2b. In one embodiment of use, bottom portions of second fasteners 111 are inserted through a respective first apertures 101 in the pair of first bodies 100a-b, and after insertion, the bottom portions of the second fasteners 111 are screwably inserted into the hard palate. During insertion of the bottom ends of second fasteners into the hard palate, the top portions of second fasteners 111 are screwed into respective threads of first apertures 101 in the pair of first bodies 100a-b until a surface portion at a top of the second fasteners 111 becomes seated against a surface portion of the first apertures 111. In one embodiment, a torque between about 0.1 and 0.6 nm is applied to the second fasteners to cause them to be inserted into both cortical bones of the palatal process of the maxilla and to achieve seating against and in the first bodies. In one embodiment, when second fasteners 111 are seated against and in the first bodies 100a-b, a fixed rigid structure is formed, which rigid structure is made even more rigid via insertion of the second fasteners into the hard palate.

In one embodiment, before insertion of the bottom end of second fasteners 111 into a hard palate, one or more spacer 50 is inserted between a hard palate facing side of the pair of first bodies 100a-b and the hard palate. The one or more spacer is intended to define a distance between the pair of first bodies 100a-b and tissue covering the hard palate. In one embodiment, the distance is 0.1-3 mm. In one embodiment of use, second fasteners 111 are screwed into the hard palate until the pair of first bodies 100a-b lightly abut against the one or more spacer 50 and such that the one or more spacer lightly abuts against tissue of the hard palate. In one embodiment, spacer 50 comprises soft silicon. In another embodiment, spacer 50 is made of material that is capable of being dissolved by fluids in the mouth. In one embodiment, spacer 50 comprises a material comprising gluten free wheat, yeast, salt and water that is formed by baking into a thin wafer that is capable dissolving very rapidly when exposed to secretions within the mouth. In other embodiments the spacer comprises resin or polycarbonate. After insertion of one or more spacer 50 and coupling of a pair of first bodies 100a-b to the hard palate, in one embodiment, the spacer is removed or is allowed to dissolve to leave an open space/air gap between the first bodies and the hard palate. In one embodiment, the space/air gap enables that no, or very minimal contact, is made between the first bodies 100a-b and the hard palate, which reduces the potential for tissue necrosis to occur. In doing so, since contact with the hard palate by the first bodies 100a-b is reduced, damage and irritation (necrosis) of the palatal soft tissue is reduced, and forces to the maxilla bone are maximized. The present invention should not be limited to formation of a space/gap via that use of the described spacer(s) as other methods can also be used, for example, via temporary anchorage of a pair of first bodies to teeth with a surgical guide so as to create the space/gap during insertion of second fasteners 111, where after creation of the space, the temporary anchorage can be removed. Further, while threadable insertion of the top ends of the second fasteners into a pair first bodies is described to rigidly couple second fasteners 111 to the bodies in a position below the palate, the present invention should not be limited to use or threads to achieve such coupling, as in other embodiments, biocompatible resins or adhesives; or clamping, locking, and interference fit type coupling mechanisms could be used to couple second fasteners 111 to a pair of first bodies in addition to, or in lieu of, the second set of threads described above.

With reference to FIG. 3, there is seen a representation of components of a skeletal anchorage expander device after a pair of first bodies has been coupled to a palate of a patient and after a first fixed aligner is removed. In one embodiment of use, after second fasteners 111 are coupled to a hard palate of a patient, first fasteners 110 are uncoupled from first bodies 100a-b, and first fixed aligner 106 is uncoupled from the pair of first bodies 100a-b and removed. After removal, it is identified that the pair of first bodies 100a-b will be separated by a distance "D" as was determined by distance "B" of first fixed aligner 106 (see FIG. 1b).

Referring now to FIGS. 4a-j, there are seen a representations of components of a skeletal anchorage expander device comprised of an adjustable aligner and/or a pair of first bodies that are configured to effectuate movement and growth of the maxillary skeletal complex of a patient. In one embodiment, a skeletal anchorage expander device of the present invention comprises an adjustable aligner 150 (see FIG. 4a). In one embodiment, the adjustable aligner 150 comprises a pair of second bodies 151a-b, where each body is coupled by at least one adjustment mechanism formed therebetween. In one embodiment, each of the second bodies 151a-b is elongated along an axis. In one embodiment, when coupled by an adjustment mechanism 152, each axis is generally parallel to the other axis. In one embodiment, the adjustment mechanism 152 comprises a double ended expansion screw having threads at both of its ends. In one embodiment, the adjustment mechanism 152 is configured to be rotated relative to the pair of second bodies 151a-b so as to cause each of the second bodies to move toward or away from each other via threaded interaction of its ends with threaded apertures in each of the second bodies. In one embodiment, each pair of second bodies 151a-b is configured with apertures dimensioned to slideably receive ends of one or more stabilizing rod 175 thereinto or therethrough. In one embodiment, each of the second bodies 151a-b comprise a plurality of threaded fourth apertures 198 configured to extend between a hard palate facing bottom side and a top side of the second bodies 151a-b. In one embodiment, fourth apertures 198 are longitudinally spaced apart to match the longitudinal spacing between second apertures 102 of each of the pair of first bodies. In one embodiment of use, adjustment mechanism 152 is rotated to a position that enables threadable first fasteners 110 to be aligned to and easily inserted through respective fourth apertures 198 of adjustable aligner 150 and into respective apertures 102 of each of the pair of bodies 100a-b. After being coupled in this manner, the pair of second bodies 151a-b will be spaced apart by the same initial distance "D" as the first bodies 100a-b are spaced apart from each other. After coupling, adjustment mechanism 152 can be used to increase or decrease the lateral distance between the pair of second bodies 151a-b, the pair of first bodies 100a-b and the first fasteners 110, which change in distance can be used to treat a maxillary deficiency of a patient by bi-laterally expanding the maxillary skeletal complex and the 9 bones that articulate with the maxilla. In one embodiment, instead of an adjustment mechanism 152 comprised of a double ended expansion screw having threads at both of its ends as described above, an adjustment mechanism 162 comprises a unilateral expansion screw (see FIG. 4d) where one end of the unilateral expansion screw is threaded and the other is not. In one embodiment, the non-threaded end is inserted into and through an aperture of one of the second bodies 151a-b and left to spin freely within the aperture, while the threaded end is coupled via its threads to a threaded aperture within the other body. The non-threaded end is secured by retainer, for example a circle-clip, at its end to limit longitudinal movement within the aperture relative to the second body. When adjustment mechanism 162 is rotated, one of the second bodies 151a-b remains fixed and the other moves. In one embodiment of use, it is identified that a skeletal anchorage expander device comprised of a unilateral expansion screw as described above can, thus, be used to treat maxillary asymmetry. Although rotation is described above to effect an increase in distance between second bodies 151a-b, it is contemplated that other mechanisms capable of causing movements of the second bodies 151a-b are within the scope of the present invention, for example a spring, a micro-motor, or some other passive or active actuator could be used to effect linear movement between the second bodies. In one embodiment, after coupling of each of the pair of first bodies 100a-b to the hard palate, a total of six fasteners will have been used, three per each first body 100a-b. Compared to use of two second fasteners per first body 100a-b, the present invention's use of three second fasteners per first body enables lessening of forces the fasteners experience during movements of the first bodies as well as lessening of forces experience by local bone supporting the fasteners. Use of more second fasteners 111 distributes the force applied to the fasteners by the resistance by the resistance of the palate to movement generated of the second bodies 151a-b and reduces the force experienced by any one fastener. Accordingly, in other embodiments, as needed or desired, to lessen forces experienced by fasteners and/or local bone supporting the fasteners, more than three second fasteners 111 and more than three apertures in first bodies to receive the fasteners are within the scope of the invention.

Figure 4A:
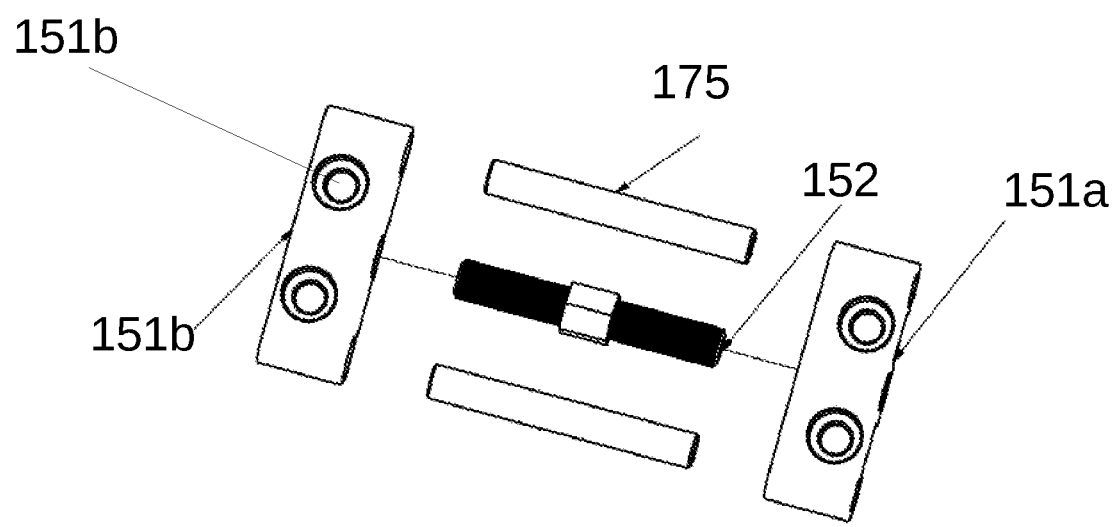
Figure 4B:
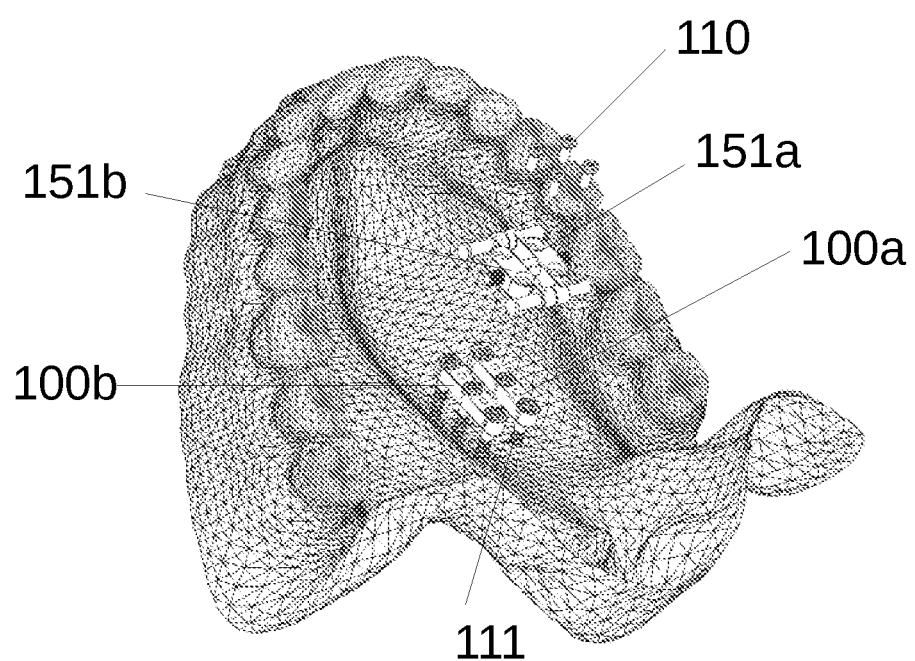
Figure 4C:
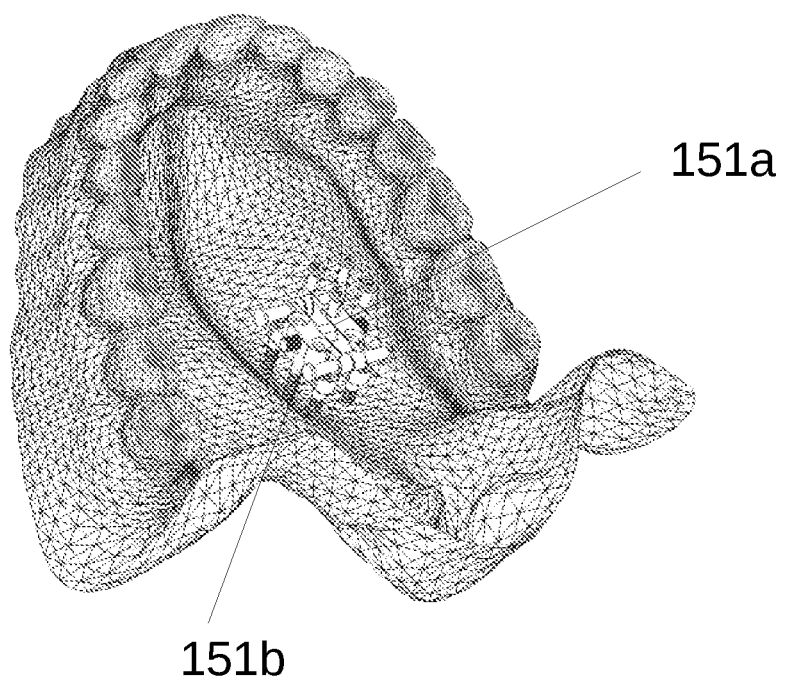
Figure 4D:
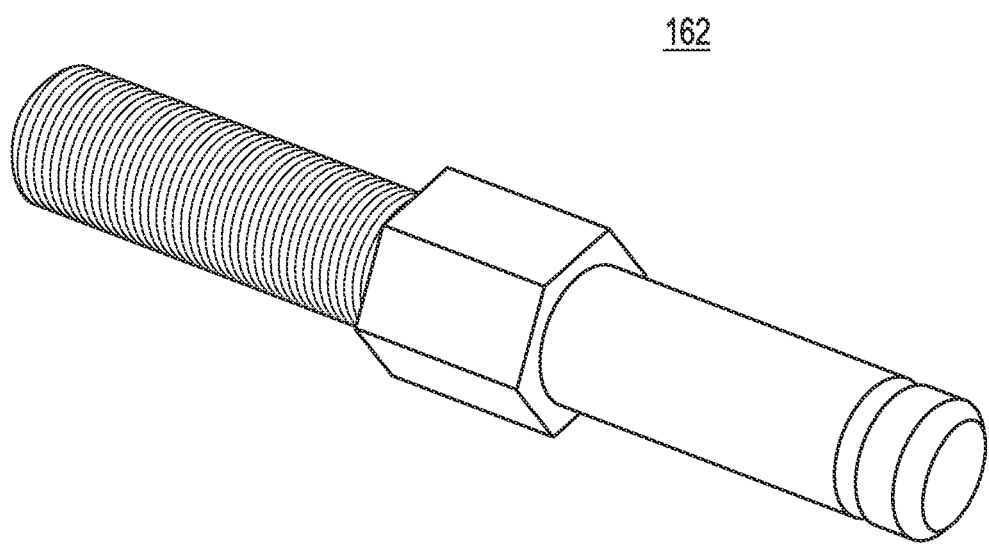
Figure 4E:
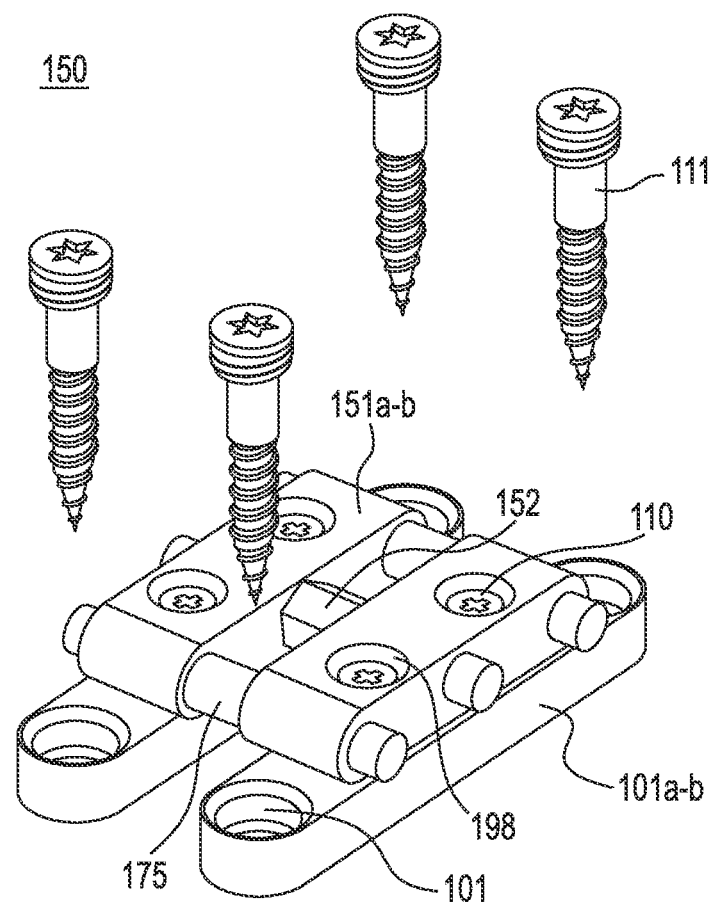
Figure 4F:
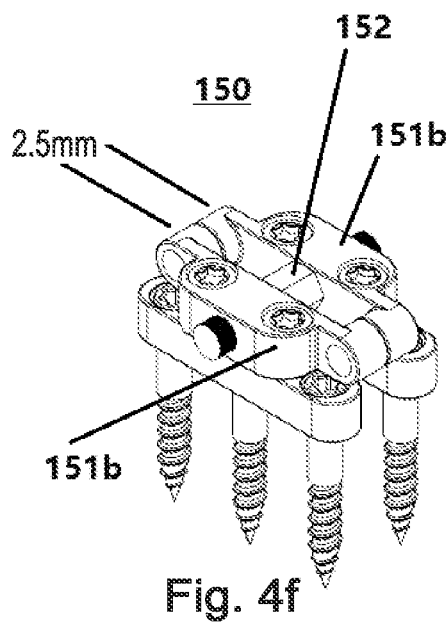

With reference to FIG. 4e, although some embodiments above described use of a fixed aligner 106 to provide initial alignment to a pair of first bodies, in one embodiment, such alignment can be provided without use of aligner 106. In one embodiment of use, threadable first fasteners 110 are inserted through respective fourth apertures 198 of a pair of second bodies 151a-b and then screwed into respective second apertures 102 of a pair of first bodies 100a-b. After being coupled in this manner, the pair of first bodies 100a-b will be spaced apart by an initial distance determined by how much expansion mechanism 152 or 162 will have been rotated. The pair of first bodies 100a-b, can thereafter be coupled to the upper palate with this initial spacing by first inserting four second fasteners 111 into first apertures 101 at both ends of the pair of first bodies 100a-b. After coupling to the upper palate, the pair of second bodies 151a-b can be removed and as desired two additional second fasteners 111 can be used to secure the pair of first bodies to the hard palate via insertion into first apertures 101 in the middle of the pair of first bodies 100a-b to. Once the first bodies 100a-b are coupled to the upper palate with a full complement of second fasteners 111, the pair of second bodies 151a-b can be recoupled to the pair of first bodies 100a-b for use via insertion of threadable first fasteners 110 into fourth apertures 198 and then via further insertion into respective second apertures 102 of the pair of first bodies 100a-b.

Figure 4G:
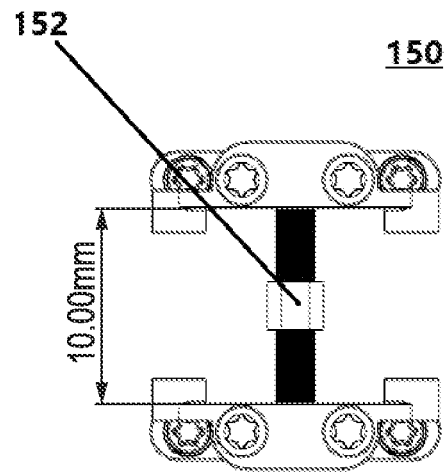
Figure 4I:
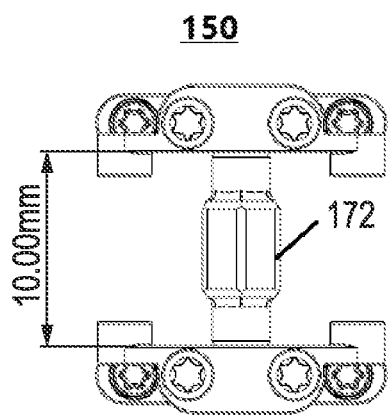
Figure 4J:
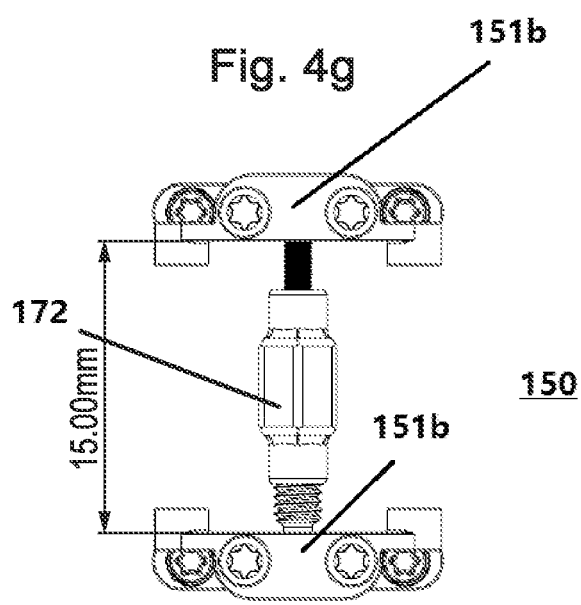

Embodiments of adjustable aligner 150 described have been found useful when an initial distance between second bodies 151a-b is desired to be minimized (see adjustable aligner 150 in FIG. 4f sans stabilizing rods 175), for example, when the first 100a-b or second 151a-b bodies are initially desired to be mounted as close to the palatal suture as possible, where in such an orientation force transmission to resisting sutural tissue is maximized. As seen in FIG. 4g, although in one embodiment adjustment mechanism 152 between the second bodies 151a-b enables a minimum distance of 2.5 mm between the second bodies to be achieved, it also determines a maximum distance 10 mm, and as well determines how far outward ends of adjustment mechanism 152 protrude outward from the second bodies in the minimized orientation in FIG. 4f. However, it is identified that in some instances, when the ends of adjustment mechanism protrude too far, the protrusion can cause interference with the anatomy of a patient's tongue or mouth. Further, when expansionary forces are applied to the second bodies 151a-b, in palates with minimal space, the bodies can begin to dig into the palatal wall tissue due to insufficient transverse space.

Figure 4H:
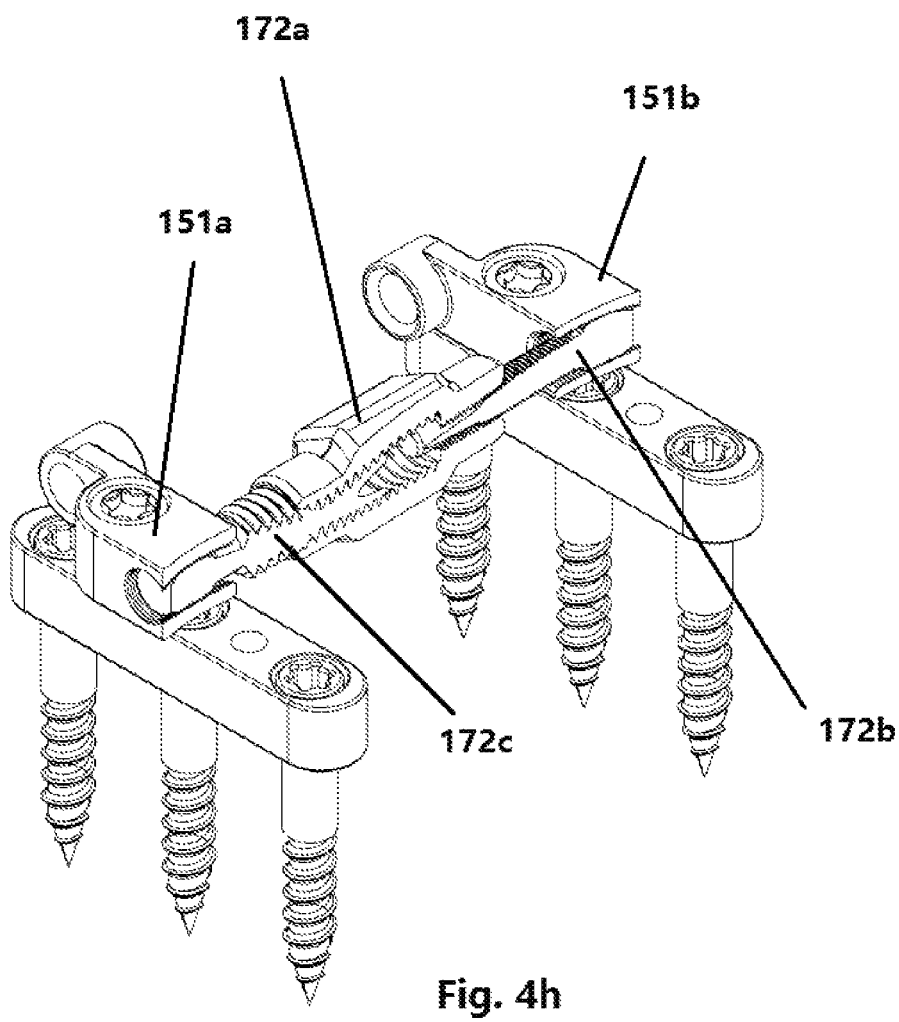

With reference to FIG. 4h, to minimize or eliminate interference with a patient's oral anatomy, in some embodiments, adjustable aligner 150 comprises an adjustment mechanism 172. In one embodiment, adjustment mechanism 172 comprises a telescopic expansion screw mechanism. In one embodiment, the expansion screw mechanism comprises a housing 172a having two threaded apertures at opposite ends and two threaded rods 172b each have a first threadable end threadably mounted in a respective threaded aperture and a second threaded end mounted within a respective threaded aperture of a second body.

In one embodiment of use, rather than using only one of adjustment mechanisms 152 or 172 to achieve a desired expansion of a patient's maxilla/palate, it may be desired to use both. For example, where an initial close placement of first or second bodies to a palatal suture is desired and a subsequent expansion greater than capable of being provided by adjustment mechanism 152 without causing interference by the adjustment mechanism is desired, an adjustable aligner 150 comprised of adjustment mechanism 152 can be used to achieve a first distance between second bodies (for example a distance of 10 mm), whereafter the first distance is achieved, and the adjustable aligner can be removed and replaced with an adjustable aligner 150 comprised of an adjustment mechanism 172 to achieve a second distance (15 mm) between the second bodies. The initial and final distances described above with regard to use of adjustment mechanism's 152 and 172 are intended to be exemplary as in other embodiments adjustment mechanisms 152 and 172 can be configured enable smaller or larger distances, for example, via appropriate selection of their lengths and/or modification of the bodies.

Referring to FIGS. 5a-b, there are seen representations of components a skeletal anchorage expander device, including of a pair of first bodies and a pair of appliances before the appliances are coupled to the pair of first bodies. In some cases, the combination of adjustable aligner 150, first bodies 100a-b, and fasteners 111 may be insufficient to achieve a clinically desired expansion of the maxilla due to very thin bone or very thick bone anatomy. Accordingly, to further reduce bone stresses by threaded fasteners, in one embodiment, a skeletal anchorage expander device of the present invention comprises a pair of appliances 120a-b. In one embodiment each appliance comprises at least one extending support 125 (see FIG. 5b). In one embodiment of use, a first end 130 of each support 125 is configured to be coupled to a respective second aperture 102 of the pair of first bodies 100a-b, and an opposite second end 131 of the supports is embedded within a respective plate 132. In one embodiment, each plate comprises acrylic or other sufficiently rigid biocompatible material as is known to be used by those skilled in the dental appliance arts. In one embodiment, when embedded within plate 132, first ends 130 of each extending support 125 are spaced apart by the same distance "Y" as are second apertures 102 of each of the pair of first bodies 100a-b. In one embodiment, each first end 130 comprises an aperture configured to receive a respective fastener 110 therethrough. In one embodiment, plates 132 are made and dimensioned from a mold or digital scan made of the mouth so that when used intraorally, they comfortably abut against the palatal tissue without any direct contact being made with any teeth.

Figure 6A:
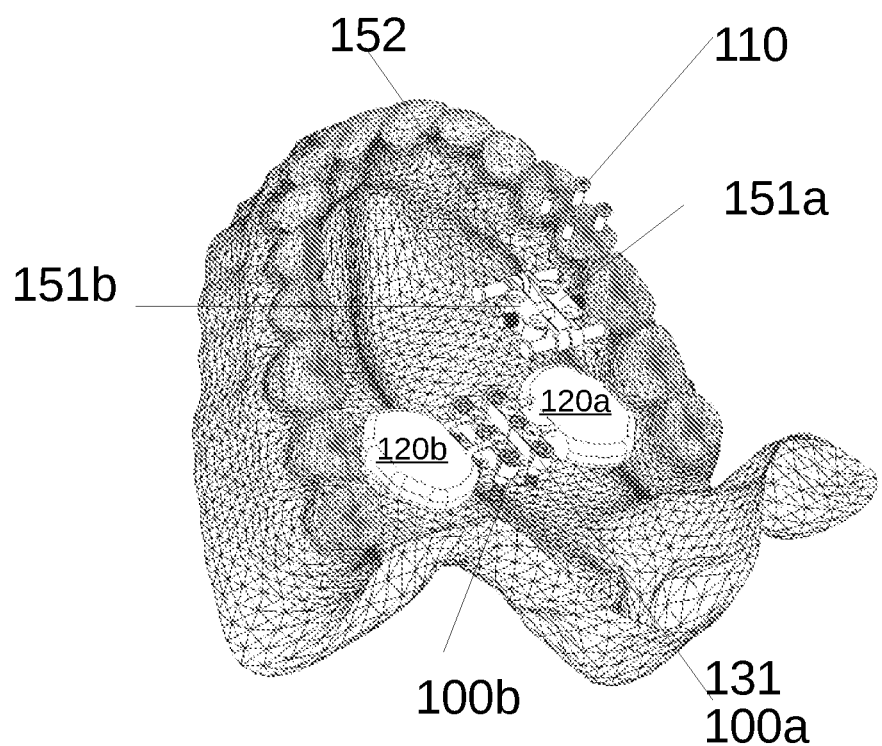
Figure 6B:
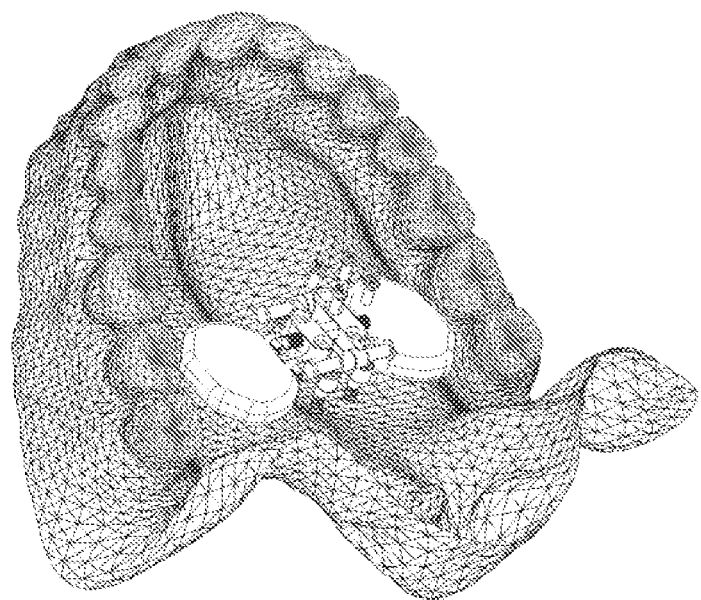
Figure 6C:
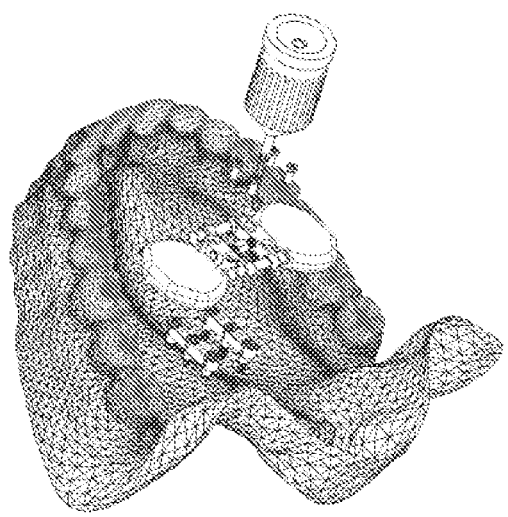
Figure 6D:
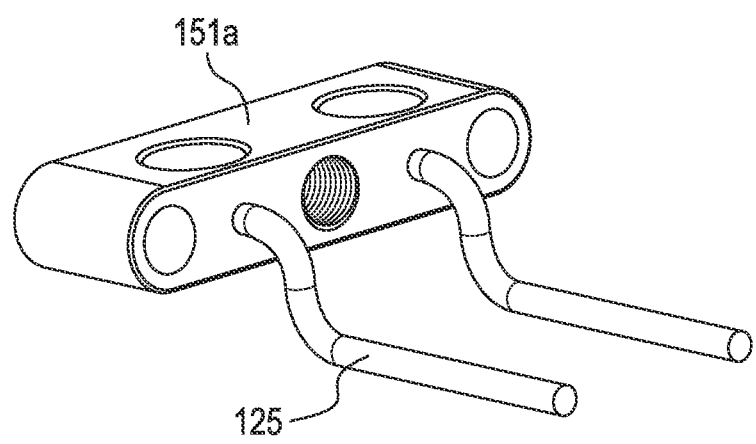

Referring to FIGS. 6a-d, there are seen representations of components of a skeletal anchorage expander device including a pair of appliances coupled to a pair of first bodies before and after an adjustable aligner is coupled to the pair of first bodies and the appliances. In one embodiment of use, threadable first fasteners 110 are inserted through respective fourth apertures 198 of adjustable aligner 150, through respective apertures in first ends 130 of extending supports 125 of appliances 120a-b (see FIGS. 6a-b), and then screwed into respective second apertures 102 of the pair of first bodies 100a-b to cause the three coupled components to form a structure that when coupled to a palate and expanded via adjustment screw 152 enables additional forces to be applied on either side of the palatal suture. In one embodiment (see FIG. 6c), rather than initially provide appliances 120a-b as units separate from that of adjustable aligner 150, each appliance is integrated to be part of respective second body 151a-b, such that the adjustable aligner 150 and each appliance can be attached to the pair of first bodies 100a-b as a single integral unit. FIG. 6d represents one such integration, where a set of first end of supports 125 is integrated into a second body and where the opposite set of ends can be molded over by a plate (not shown).

Referring to FIGS. 7a-b, there are seen representations of components of a skeletal anchorage expander device comprised of appliances before and after a distance between an adjustable aligner is increased by an adjustment mechanism. In one embodiment of use, adjustable aligner 150 is coupled to a pair of first bodies 100a-b and a distance between the pair of second bodies 151a-b is increased via rotation of adjustment mechanism 152, which increase causes a distance between the first bodies 100a-b and appliances 120a-b to be increased. In embodiments, the increase is effected via use of a spanner wrench, activation key, or other device configured to move or rotate adjustment mechanism 152/162. In one embodiment, an incremental increase in a distance between second bodies 151a-b causes lateral expansion of the maxilla of a patient, where the amount of increase is determinative of the amount of potential expansion and that can be achieved. During use of adjustable aligner 150, it is identified that portions of second fasteners 111 at their insertion point into the hard palate are exposed by the small space/gap created between the hard palate and the pair of first bodies 100a-b (see use of spacer 50 to create space/gap in discussion of FIG. 2 above). Compared to if the small space did not exist, the existence of a space causes an increase in the amount of stress the second fasteners are subject too at their insertion point into the hard palate via the aforementioned resistance to movement by the palatine suture at one end of the second fasteners and the movement applied by the second bodies 151a-b at the other end of the fasteners. The stresses applied to the fasteners 111 implies the hard palate at each of the insertion points will also be subject to the stress. A reduction of local stresses applied to fasteners 111 and the maxilla bone is thus identified as being desired. One approach to reduce fastener stress includes distributing the stress over more fasteners as discussed above. However, when appliances 120a-b are also used, since their plates 132 abut against the palate, expansion of the second bodies 151a-b will cause the plates to apply forces to the soft palate and thus the hard palate which forces can be used to at least partially overcome the resistance to expansion by the maxilla, which in turn can be used to further reduce stresses experienced by the fasteners. Threadable insertion of the top ends of the second fasteners 111 into respective threaded apertures of the pair of first bodies 100a-b, the use of more than two second fasteners 111 per first body, and the use of appliances as described above can be used alone or in combination to provide stability of the pair of first bodies 100a-b and second bodies 151a-b such that molar and tooth borne anchorage devices do not necessarily need to be used. By eliminating force transmission to the teeth, many benefits are derived, namely, greater orthopedic effects occur relative to alveolar or tooth effects. Greater orthopedic effects are correlated with greater airway and aesthetic benefits. Moreover, many risks are eliminated by the non-involvement and contact with the teeth, including root resorption, tooth tipping, and potentially a scissors bite. Although non-involvement and contact with teeth is preferred, it should be understood that nothing precludes embodiments of the present invention described above or further below from being coupled to the teeth when desired or needed to achieve a particular clinical outcome.

Referring to FIG. 8, there are seen representation of a pair of first bodies after a distance between the adjustable aligner is increased by a clinically desired amount the adjustable aligner and appliances are removed. In one embodiment of use, after a distance between a pair of first bodies 100a-b is increased to a clinically desired distance "D2", first fasteners 110 are unscrewed, and adjustable aligner 150 and, if used, appliances 120a-b are removed. In one embodiment, to enable regrowth of the palatine suture while distance "D2" is maintained, a pair of third bodies 170a-b are positioned over the pair of first bodies 100a-b. In one embodiment, each of the third bodies 170a-b comprise a plurality of fifth apertures 195 each being longitudinally spaced apart with the same spacing as the second apertures 102 of each first body. In one embodiment, apertures 195 extend from a palatal facing side to a top side of the pair of third bodies 170a-b and are configured to receive fifth fasteners 191 therethrough.

Referring to FIG. 9, there are seen representations of a pair of first bodies and a pair of third bodies after the pair third bodies 170a-b are coupled to the pair of first bodies via respective fifth fasteners 191 being inserted into respective fifth apertures 195, and the respective fifth fasteners being screwed into respective second apertures 102 of the pair of first bodies 100a-b to couple the third bodies to the first bodies.

Referring to FIGS. 10a-d, there are seen representations of components of a skeletal anchorage expander device, including a second fixed aligner. In one embodiment of use, to maintain distance "D2" while first bodies 100a-b and third bodies 170a-b are coupled together, a second fixed aligner 196 is used. In one embodiment second fixed aligner 196 comprises a body configured with a shape that maintains distance "D2" over a holding/stabilizing phase during which a palatine suture of a patient is allowed to regrow with bone and to maintain the distance "D2" on its own and without use of embodiments of the present invention. In one embodiment, second fixed aligner 196 is configured to couple third bodies 170a-b together. In one embodiment, second fixed aligner 196 comprises a wire bent into a shape that allows insertion of its ends 166 and 167 into respective sixth apertures 197 formed in each of the pair of third bodies 170a-b. In one embodiment, second fixed aligner 196 is manufactured as a single piece from stainless steel spring metal. In one embodiment, second fixed aligner 170a-b is manufactured of a material that is sufficiently strong enough to maintain distance 'D2" during the holding/stabilizing phase. Use of fixed aligner 196 during the holding/stabilizing phase instead of an adjustable presents a far sleeker and less bulky apparatus that enables greater tongue volume and tongue posture during the phase. Furthermore, removal of the adjustable aligner after an achieved expansion enables greater hygiene and sanitation. In other embodiments, however, after an achieved expansion, the adjustable expander can be left in place with no further adjusts being made to effectively function as a fixed aligner.

Referring to FIGS. 11a-b there are seen representations of a skeletal anchorage expander device comprised of additional bodies. In some embodiments, during expansion of a patient's maxillary complex, a patient's age, gender, bone density, or a desired clinical outcome may require an amount of stability that some of the embodiments described above are not best suited to provide. Accordingly, in one embodiment, a skeletal anchorage expander is provided with at least two additional bodies 165. In embodiments, bodies 165 comprise extending arms, rods, stiff wires or other structures configured to provide additional points of stability to the skeletal anchorage expander without reliance on support of the teeth. In one embodiment, at least one body extends laterally from each of first bodies 100a-b (see FIG. 11a) or from each of second bodies 151-a-b (see FIG. 11b). In one embodiment, one end of each body 165 is integrated with first bodies 100a-b or second bodies each body 165, and another end comprises an attachment mechanism 164 configured to provide a coupling to the hard palate. In one embodiment, each attachment mechanism is configured to receive a fastener 163 configured to provide releasable coupling of the attachment mechanism to the hard palate. In embodiments, fastener 163 can comprise screws, rivets, pins, interference type mechanism biocompatible adhesives or other dental fasteners known in the arts. Use of bodies 165 provides additional coupling points via which forces can be distributed across more points of attachment of a skeletal anchorage device to the palate.

Referring to FIGS. 12a-c, there are seen representations of a skeletal anchorage expander device that does not necessarily rely on the use of a pair of first bodies. In one embodiment, a skeletal anchorage expander comprises an adjustable aligner 151 or a fixed aligner 106. In one embodiment, a skeletal anchorage expander comprises a plurality of sixth fasteners 136. One bottom end of each sixth fastener 136 is configured to be inserted into the maxilla and an opposite top end is configured to receive and be coupled to a fixed aligner 106 or an adjustable aligner 150. In one embodiment, a respective alignment and spacing of each sixth fastener 136 relative to other sixth fasteners that are coupled to a patient's hard palate is determined by spacings of apertures formed through fixed aligner 106. In one embodiment, top ends of sixth fasteners 136 are initially coupled to fixed aligner 106 via interference fitment with recesses formed in the bottom of the apertures formed in the fixed aligner 106, where after fitment each sixth fastener extend from and is aligned with the apertures. In one embodiment of use, the fixed aligner 106 and sixth fasteners 136 are aligned to and positioned against the palate so that an equal number of sixth fasteners 136 are positioned on either side of the palatine suture. In one embodiment of use, each fastener is subsequently coupled to the hard palate. In one embodiment, the bottom end of each sixth fastener 136 comprises threads that are inserted into the hard palate via rotatable interaction with the top ends of each fastener thorough the apertures in fixed aligner 106. In one embodiment of use, after insertion of each sixth fastener 136 to a desired depth, fixed aligner 106 is decoupled from sixth fasteners 136 via removal of the top ends of the sixth fasteners from the recesses in the apertures of fixed aligner. In one embodiment of use, an adjustable aligner 150 is coupled to the sixth fasteners 136. In one embodiment, attachment mechanisms are provided with or in each second body 151a-b and are dimensioned to be longitudinally spaced apart with the same longitudinal spacing as the apertures of fixed aligner 106. In one embodiment, before coupling sixth fasteners 136, the second bodies 151a-b are spaced apart using an adjustment mechanism 152 to provide the attachment mechanism in the second bodies 151a-b with the same lateral spacing as that of the apertures of fixed aligner 106. In one embodiment, each attachment mechanism in adjustable aligner 150 is configured such that when adjustable aligner 150 is placed over sixth fasteners 136, the attachment mechanism retains adjustable aligner 150. In embodiments, the attachment mechanisms comprise, apertures, snap fit mechanisms, interference type mechanisms, adhesive or combinations thereof that are configured to allow sixth fasteners 135 to be coupled and decoupled to the adjustable aligner 150. In one embodiment, attachment mechanisms comprise apertures and seventh fasteners 135 that are provided in and with each second body 151a-b, where seventh fasteners comprise fasteners and where top ends of sixth fasteners 136 are provided with apertures to receive bottom ends of seventh fasteners 135. In one embodiment top ends of sixth fasteners 136 and bottom ends of seventh fasteners 135 are threaded. In one embodiment of use, after adjustable aligner 150 is positioned over sixth fasteners 136, seventh fasteners 135 are inserted into apertures of adjustable aligner and coupled to sixth fasteners 136. Subsequently, adjustable aligner 151 can be used to generate therapeutic expansionary forces to alignably installed sixth fasteners 136, without the need to use first bodies 100a-b described above. Further, in as much as sixth fasteners 135 can be installed into the palate to a desired depth, in one embodiment, installation may be performed such that the top ends of the sixth fasteners 135 can protrude a particular distance below the palate, in which case, one or more spacer 50 as described above may not be needed to achieve a desired mounting space/gap between adjustable aligner 150 and tissue of the palate. Although four sixth 136 and seventh 135 fasteners are represented by FIGS. 12a-b, other numbers of fasteners and attachment mechanism are understood to be capable of implementation and use, for example, six or more sixth and seventh fasteners, and respective six or more attachment mechanisms can used as may be desired or needed to distribute forces experienced by the fasteners.

Referring to FIG. 13, there are seen representations of another embodiment of a skeletal anchorage expander device that does not require use of first bodies 100a-b.

In another embodiment, where a pair of first bodies 100a-b discussed above need not be used, each of the second bodies 151a-b comprise a plurality of threaded fourth apertures 198 that are configured to extend between a hard palate facing bottom side and a top side of the second bodies 151a-b. Although four threaded apertures 198 are discussed herein, the present invention contemplates other numbers of fourth apertures can be implemented within each of the second bodies 151a-b to better distribute forces and decrease screw and bone stress. In one embodiment of use, pair of second bodies 151a-b are first coupled to the upper palate by inserting bottom ends second fasteners 111 into fourth apertures 198, and after insertion the bottom ends of the second fasteners 111 are screwably inserted into the hard palate. During insertion of the bottom end into the hard palate, the top end of second fasteners 111 are screwed into respective threaded fourth apertures 198 in the pair of second bodies 151a-b. In one embodiment, before full screwable insertion of the second fasteners 111 into the palate, a spacer 50 may be used to create a distance between the pair of second bodies 151a-b and the palate. In one embodiment, when used without the pair of first bodies as described above, the pair of second bodies 151a-b can be coupled to or comprise an appliance, arm, rod, stiff wire or other structure configured to provide additional points of stability to the skeletal anchorage expander as described above.

Comparison of a prior art device against various embodiments of the present invention were performed, including for:

Prior Art device: an expander assembly coupled to the teeth via molar bands and to the palate via 4 fasteners each comprised of a single set of thread configured to be threadably inserted into the palate (i.e. Moon device referenced in Background)

Embodiment 1: An expander assembly using an adjustable aligner 150 coupled to the palate via a pair of first bodies 100*a-b* and six fasteners 111, where each fastener comprises two sets of threads, and where one set of threads is threadably coupled to the pair of first bodies and the second set of threads is threadably coupled to the palate (see FIG. 2*b*).

Embodiment 2: An expander assembly using an adjustable aligner 150 coupled to the palate via a set of two bodies 120*a-b* (see FIG. 6*b*) and a pair of first bodies 100*a-b* and six fasteners 111, where each fastener comprises two sets of threads (see FIG. 2*b*), and where one set of threads is threadably coupled to the pair of first bodies and the second set of threads is threadably coupled to the palate (see FIG. 2*b*).

The following peak bone stresses were noted:
Prior Art device: 98 MPa
Embodiment 1: 84 MPa (provided reduced stresses to fasteners and bone compared to prior art).
Embodiment 2: 50 MPa (provided reduced stresses to fasteners and bone compared to prior art).

The following peak palatine strains were noted:
Prior Art device: 0.479
Embodiment 1: 0.426 (provided more uniform strain to the palatine suture compared to prior art).
Embodiment 2: 0.397 (provided more uniform strain to the palatine suture compared to prior art and embodiment 1).

Referring to FIG. 14, there is seen a representation of a third fixed fastener. In one embodiment, a third fixed aligner 1901 comprises a surgical guide that is configured to accurately position and fixate a pair of first bodies 100*a-b* to the palate on either side of the palatal suture.

In one embodiment, a cast of a patient's intra-oral geometry is obtained, a mold is made from the cast, and an appliance is made from the mold in the form of a third fixed aligner 1901 that has matching features of the patient's palate, jaw and/or dentition formed in its palate facing surface. In another embodiment, a digital scan (for example, a palatal and/or a CBCT scan of the upper jaw) is performed via a computer-controlled imaging device and a representation of the patient's palate, jaw and/or dentition is obtained and stored in memory (for example, as an STL file). The stored representation can subsequently be used by a 3d printing or machining device to form a third fixed aligner 1901 that has matching features of the patient's plalate, jaw, and/or dentition formed in its palate facing side. In one embodiment, fixed aligner comprises bio-compatible material suitable for oral use as is known to those skilled in the art. In one embodiment, third fixed aligner 1901 comprises apertures 1936 that are formed in the third fixed aligner 1901 to guide insertion of second fasteners 111 into the hard palate. In one embodiment, apertures 1936 are formed along a peripheral notch 1937 formed in the third fixed aligner that is configured to receive first bodies 100*a-b*. In one embodiment of use, after installation against a patient's soft palate, third fixed aligner 1901 is used to guide first bodies 100*a-b* and fasteners 111 into a position on either side of a palatine suture and such that fasteners 111 can be rotated into the hard palate until threads at their top become fixed in and against the pair of first bodies. In one embodiment, insertion of dentition portions of third fixed aligner 111 against dentition of a patient can be used so that movement of the first bodies 100*a-b* with respect to the maxilla is minimized during insertion of fasteners 111. In one embodiment of use, third fixed aligner 1901 is to define a space/gap between the first bodies 100*a-b* and the palate. To achieve a desired space/gap, third fixed aligner 1901 can be manufactured with a thickness in the area around apertures 1936 according to a particular desired space/or gap, for example, with a space/gap between about 0.1 mm and about 3 mm. Third fixed aligner 1901 can be made from a relatively rigid, but frangible material, for example, biocompatible acrylic, resin, or polycarbonate. In one embodiment, third fixed aligner 1901 is provided with one or more thinned region 1938 that enable removal of the fixed aligner via subsequent breakage of the aligner along of the thinned region(s) so that the broken pieces of the aligner can be removed from around the fasteners and under the pair of first bodies 100*a-b* and so the aligner can be removed without removing or loosening fasteners 111.

Referring to FIGS. 15*a-c*, there is seen a representation of another third fixed fastener. In one embodiment, a third fixed aligner 2001 is manufactured using techniques discussed above with reference to third aligner 1901. In one embodiment, third fixed aligner 2001 comprises alignment features 2117 configured to receive a pair of first bodies 2100*a-b*, and a plurality of apertures 2119 configured to receive a plurality of fasteners, including fasteners 2116 and fasteners 2111. In one embodiment, the plurality of apertures 2119 comprise apertures that are configured with a spacing that match spacings of respective apertures 2115 in first fixed aligner 2106 and the first bodies 2100*a-b*. In one embodiment of use, first bodies 2100*a-b* are positioned against and/or in features 2117 on one side of third fixed aligner 2001, first fixed aligner 2106 is positioned against an opposite side of the third fixed aligner 2001, and fasteners 2116 are inserted in apertures 2115, through apertures 2119, and into apertures in the first bodies to join the first bodies and the first fixed aligner together so as to form an assembly where the third fixed aligner is sandwiched between the pair of first bodies and the first fixed aligner. In one embodiment of use, the assembly is subsequently positioned against the palate and a plurality of fasteners 2111 are used to secure the assembly to the palate. In one embodiment of use, third fixed aligner 2001 comprises a thickness T1 in an area configured to receive the first bodies 2100*a-b* in features 2117, where the thickness T1 is thicker than a thickness T2 of the pair of first bodies 2100*a-b*, and such that a palatal facing side of the first bodies 2100*a-b* in an assembly mounted to the palate is spaced apart from the palate by distance determined by a difference between the thickness of the third fixed aligner 2001 and the thickness of the pair of first bodies, for example, a distance of about 0.1 mm and 3 mm.

In one embodiment, third fixed aligner 2001 and first fixed aligner 2106 comprise apertures 2139 that are configured with dimension that allows the plurality of fasteners 2111 be received entirely therethrough and such that subsequently the second fixed aligner 2106 and the third fixed aligner 2001 can be removed via removal of fasteners 2116 while leaving the pair of first bodies 2100*a-b* secured to the hard palate via fasteners 2111 in a configuration that the pair of first bodies are spaced apart from the palate by a distance and such that an adjustable aligner 150 can be coupled thereto. In one embodiment, third fixed aligner 2001 is configured to fixate to a patient's dentition, and to be sandwiched between first bodies 2100a-b and fixed aligner 2106 so as to position the bodies against a particular location in a patient's mouth. The thickness of and counterbores formed in first bodies 2100a act to further align fasteners 2111 to enable a precise mounting of first bodies 2100a-b above the palate and of fasteners 2111 into the hard palate.

Referring to FIGS. 16a-d, there are seen representations of another skeletal anchorage device. In some embodiments, it may difficult to secure certain embodiments described above in a patient's mouth due to a "v" shaped, narrow, or constricted palate, where in palates of these and other shapes, the vertical orientation of the threadable second fasteners 111 with respect to the palate may be difficult to secure in place due to the limited flat surface area.

In one embodiment a skeletal anchorage device comprises a pair of first bodies 100c-d (see FIG. 16b-c). In one embodiment (see FIG. 16a), the pair of first bodies 100c-d each comprise second apertures 102 that define longitudinal channels that are angled (instead of being parallel) with respect to longitudinal channels that define first apertures 101. This allows the pair of first bodies 100c-d to be secured to a pair of second bodies 151a-b in a similar manner as described with other prior embodiments, but where the axis of threadable second fasteners 111 inserted within second apertures 102 of one of the pair of first bodies 100c-d will be oriented at an angle with respect to the longitudinal axis of second fasteners inserted in the other of the pair of first bodies. In one embodiment, extensions 173 may be provided to the first bodies 100c-d to provide additional structural support for second apertures 102. In one embodiment, the pair of first bodies 100c-d with the extensions 173 comprise a unitary element. In other embodiments, the first bodies 100c-d and the extensions may be coupled together through various attachment means. It should also be noted that inserting the screws at an angle may allow for more surface contact in the bone than a vertical screw. Moreover, an angled screw can be designed to insert through the mid palatal suture in a different way than a vertical screw, which may be desirable) Although in the embodiments of FIGS. 16a-c the first bodies are configured to mate with second bodies along extension portions 173 of a top surface that are not parallel to bottom surface of the first bodies, in other embodiments the extension portions can be eliminates such that top surfaces and bottom surfaces of first bodies are substantially flat and/or parallel to each other (see FIG. 16d).

In one embodiment, as may be determined by a particular patient's palate shape and anatomy the angle of the longitudinal axis of second apertures 102 with respect to the longitudinal axis of first apertures 101 in each body 100c-d may comprise between about zero (0) and about ninety (90 degrees). In other embodiments, the angle of the longitudinal axis of second apertures 102 with respect to the longitudinal axis of first apertures 101 is between about one (1) and about sixty (60) degrees. In one embodiment, the angle of the longitudinal axis of second apertures 102 with respect to the longitudinal axis of second apertures in one of the pair of second bodies 100c-d may be the same as the angle in the second of the pair of first bodies 100c-d. In one embodiment, the angle of the longitudinal axis of second apertures 102 with respect to the longitudinal axis of second apertures in one of the pair of second bodies 100c-d may be the different from that of the angle in the second of the pair of first bodies 100c-d.

Although the embodiments discussed and described above have so far been directed to devices and methods used to apply transverse forces to treat maxillary deficiencies, the present invention identifies that one or more of the embodiments can be used to apply forward protraction forces to treat maxillary deficiencies.

In embodiments above, it was identified that a pair of second 151a-b or third bodies 170a-b can be coupled to a pair of first bodies 100a-b, where in one embodiment, apertures 197 in the pair of third bodies 170a-b are configured to be coupled to a spring wire 196 (see FIG. 10b) that is used to maintain a lateral distance between palatine sutures of the maxilla. As seen in embodiments below, the second and third bodies can also be configured to comprise apertures that can be intraorally coupled to an externally worn appliance, for example an orthodontic face bow, that can be used to enable forward movement and growth to the maxilla. In one embodiment, the appliance transfers one or more extra-oral protraction force to bodies mounted intraorally to a patient's maxilla in a manner that does not cause downward forward directed movement and growth of the maxilla, or equivalently only forward growth, or a combination of forward and upward movement and growth.

Referring to FIGS. 17a-c, there are seen representations of an orthodontic device comprised of a pair of third bodies and an externally worn appliance coupled to the pair of bodies. In one embodiment (FIG. 17a below), a pair of third bodies 2170a-b are coupled to a palate via a pair of intervening first bodies 2100a-b (not shown as they are underneath third bodies 2170a-b in FIG. 17a). In one embodiment, each of the pair of third bodies 2170a-b is configured to mate with each free end of appliance 2002 (represented by 2002a-d). In one embodiment, mating is achieved via insertion of free male ends of appliance into female apertures 2197 of the pair of third bodies. In embodiments, mating can be maintained via a fastener, an interference fit, snap fit, slip fit, and/or or other releasable coupling formed between the pair of third bodies 2170a-b and free ends of appliance 2002. In some embodiments, apertures 2197 enable quick and simple coupling and removal of appliance 2002 to and from the pair of first bodies 2100a-b. In some embodiments, appliance 2002 is manufactured from one or more stainless steel, ceramic, cobalt chrome or other sufficiently strong material.

In another embodiment, a pair of second bodies 2151a-b are coupled to a hard palate via intervening first bodies 2100a-b. In one embodiment, each of the pair of second bodies 2151a-b is configured to mate with each free end of an appliance 2002. In embodiments, mating can be maintained via a fastener, interference fit, snap fit, slip fit, or releasable coupling formed between the pair of second bodies 2150a-b and the free ends of appliance 2002. In one embodiment, mating is achieved via insertion of free male ends of appliance 2002 to into female apertures 2197 formed in the second bodies.

Referring to FIG. 18, there is seen a representation of a pair of first bodies coupled to an externally worn appliance. In one embodiment, rather than couple an appliance 2002 to second 2151a-b or third bodies 2170a-b, the appliance is coupled to a pair of first bodies 2100a-b via fasteners 2198 provided to or in the first bodies. In one embodiment, first bodies 2100a-b comprise apertures similar to apertures 2197 described above.

Referring back to FIG. 17a, in one embodiment, appliance 2002 comprises two first portions 2002a that are configured in a shape that extends laterally away from each free end to behind each of a patient's most posterior teeth (for example, molars), where after extending past the posterior teeth, the two first portions 2002a are configured to join to third portions 2002c by bent portions 2002b, where the third portions 2002c are configured in a shape that extends from the bent portions generally along and opposite outer surfaces of a patient's teeth and out the patient's mouth, where outside the patient's mouth, the two third portions 2002 are configured to be joined together, either in the form of an integral or non-integral fourth portion 2002d, or directly. In another embodiment, instead of extending laterally behind distal teeth, first portions 2002a can be configured in a shape that allows them to fit between spaces present between the teeth. In other embodiments, the shape of one or more portions of appliance 2002 an be customized to match a patient's particular geometry.

Referring to FIGS. 19a-b, there are seen other representations of an externally worn orthodontic appliance. In one embodiment, appliance 2002 comprises a fifth portion 2002e. In one embodiment, the fifth portion is coupled to, and extends centrally from fourth portion 2002d in a generally orthogonal and upward direction relative to the fourth portion. In one embodiment, fifth portion 2002e is coupled to fourth portion 2002d via a rigid connection, for example, via brazing, welding, or other fixed coupling mechanism know to those skilled in the art. In one embodiment, fifth portion 2002e is configured with two branches that extend upward from the fourth portion 2002d and that rejoin together above the fourth portion 2002d in a manner that an aperture is defined by and such that the two rejoined branches extend to a terminating end. In one embodiment, the fifth portion 2002e comprises at least one force application point 2002n in the form of a hook, ring (see FIG. 19a), indentation (see FIG. 19b), or other attachment mechanism to which elastics or other external force applicators from externally worn protraction frames or devices can be coupled. In one embodiment, fifth portion 2002e is configured such that it extends upward such that little or no interference occurs with a patient's nose during use.

Referring to FIGS. 20a-b, there is seen a representation of external forces applied to an externally worn appliance. As identified by the present inventors, when external protraction forces are coupled to an appliance, and by the appliance to a pair of bone anchors mounted to the maxilla, application of forward or forward and upward forces to the appliance may be used to achieve substantially only forward growth, or forward and upward growth, wherein such forces preferably do not generate or minimally generate rotational moments about the attachment points of the bone anchors to the maxilla. The present invention identifies that when forward, or forward and upward protraction forces are applied to an appliance that is coupled to a pair of bodies coupled to a maxilla at a hard palate location, forward or substantially forward movement and growth of the maxilla can also be achieved when rotational moments at the pair of first bodies 2100a-b where they are coupled to the maxilla are eliminated or substantially minimized. The present invention identifies that rotational moments transferred to the pair of bodies and, thus, the maxilla can be substantially minimized or eliminated when extra-oral forces are applied to a appliance in a direction that passes through the force application points on the appliance (for example see points A, B, and/or C) and a pair of bodies (for example, see first bodies 2100a-b in FIG. 20a) coupled to the maxilla (for example, the hard palate). In one embodiment, with reference to a standing patient whose skull face forward, and with 1588 gm of force applied to an appliance along an axis passing at an angle of 60 degrees with respect to the horizontal and through an application point "C" on the appliance and through a point "D" on a pair of first bodies, desired forward only growth and movement of a patient's maxillary complex can be achieved. Depending on a particular patient's skeletal geometry and/or a particular amount of desired movement or growth of a patient's maxilla, other forces, angles and other locations on the appliance are also within the scope of the invention as long the direction of force(s) applied to the appliance are aligned to a pair of bodies according to the embodiments described above. For example, as shown in FIG. 20b, protraction forces can potentially be applied to a fifth portion 2002e at other locations 2002n, as long as the forces are applied in a direction that passes generally centrally through the pair of first bodies and the force application point on the appliance.

Referring to FIGS. 21a-b, there is seen another representation of an externally worn orthodontic appliance and its use. In one embodiment, each third portion 2002c of appliance 2002 extends generally along and opposite outer surfaces of a patient's teeth and is formed of an intra-oral portion 2002p and an intraoral/extra-oral portion 2002q coupled to intra-oral portion 2002p by a releasable joint 2002f, for example, via a releasable joint formed by one or more of hooks, rings, snap fits, slip fits, interference fits, and/or other similar interlockings formed at ends of the intra-oral and intraoral/extra-oral portions. In one embodiment, during intra-oral use of appliance 2002, as needed or desired (for example, during periods when an external head gear and appliance may not be desired to be worn in public) intraoral/extra-oral portions can be decoupled from intra-oral portions via a releasable joint 2002f. Although, FIGS. 21a-b represent an appliance joined at one joint 2002f on each of its sides, it is understood that in other embodiments, an appliance could comprise more joints, and thus more releasable portions than are represented.

Thus, when using pairs of first 2100a-b, second 2151a-b or third bodies 2170a-b with an orthodontic appliance 2002, it identified that in addition to lateral expansion and growth of a maxilla, forward or a combination of forward and upward movement and growth of a patient's maxilla can also be achieved. In an embodiment where third bodies 2170a-b are used, it is further identified that in addition to bilateral movement and growth, unilateral movement and growth of the maxilla can also be achieved. It is also identified that use of pairs of first 2100a-b, second 2151a-b and third bodies 2170a-b obviates the need to perform invasive surgical procedures such as those needed by other devices. It is further identified that aspects of the present invention are well suited for use of an externally worn appliance by a sleeping patient since it can be configured with shapes that span only above and across a patient's frontal facial anatomy and that only minimally interferes sleeping on the side.

The preceding embodiments have been described in some detail to facilitate understanding, the described embodiments are to be considered illustrative and not limiting. It will be apparent to one of ordinary skill in the art that certain changes and modifications can be practiced within the scope of the appended claims.

For example, one or more features from any embodiment may be combined with one or more features of any other embodiment without departing from the scope of the disclosure. Further, modifications, additions, or omissions may be made to any embodiment without departing from the scope of the disclosure. Additionally, other dimensions and other materials other than those disclosed can be used as long as they are compatible and sufficiently robust for human use. Also, although embodiments of the present invention are described to enable use without necessarily requiring coupling to dental or molar band, it should be understood that such use is not precluded and the present invention could, if desired, be adapted for use with such devices. Further, although embodiments of the present invention have been described with respect to use as a orthodontic device to treat orthodontic conditions, their use is much greater, for example as a medical device that can be used to treat non-obese obstructive sleep apnea caused by maxillary hypoplasia, or for use with other surgical procedures capable of being performed by a craniomaxillofacial surgeon, which procedure could be covered by medical insurance rather than just by dental insurance.

What is claimed is:

1. A maxillary expander, comprising:
    (i) first bodies, having first apertures and second apertures,
    (ii) bone screws configured to screw into the hard palate and configured for insertion into the first apertures,
    (iii) first fasteners configured to be threadably screwed into the second apertures, and
    (iv) an adjustable aligner, including
        (a) second bodies, configured to couple to the first bodies, and
        (b) an adjustment mechanism configured to cause the second bodies to move away from each other, to thereby cause the first bodies to move away from each other when coupled to the second bodies,
        wherein the adjustable aligner may be coupled and uncoupled from the first bodies while the bone screws are screwed into the hard palate, and
        the second bodies have third apertures configured to receive the first fasteners.

2. The maxillary expander of claim 1, wherein:
    each of the first bodies comprises 3 of the first apertures and 2 of the second apertures, and
    each of the second bodies comprises 2 of the third apertures.

3. The maxillary expander of claim 1, wherein:
    the first apertures have an axis along openings of the apertures,
    the adjustment mechanism has an axis along a direction of expansion, and
    the axis along openings of the apertures is substantially perpendicular to the axis along the direction of expansion.

4. The maxillary expander of claim 1, wherein the first apertures are counter sunk to receive the upper end of the bone screws.

5. The maxillary expander of claim 1, wherein the adjustment mechanism is configured to rotate relative to the second bodies to cause the second bodies to move toward or away from each other.

6. The maxillary expander of claim 5, wherein:
    each of the first bodies comprises 3 of the first apertures and 2 of the second apertures, and
    each of the second bodies comprises 2 of the third apertures.

7. The maxillary expander of claim 5, wherein:
    the bone screws comprise a threaded upper end, and
    the first apertures are threaded to receive the threaded upper end of the bone screws.

8. The maxillary expander of claim 3, wherein:
    each of the first bodies comprises 3 of the first apertures and 2 of the second apertures, and
    each of the second bodies comprises 2 of the third apertures.

9. The maxillary expander of claim 4, wherein:
    each of the first bodies comprises 3 of the first apertures and 2 of the second apertures, and
    each of the second bodies comprises 2 of the third apertures.

10. The maxillary expander of claim 4, wherein:
    the bone screws comprise a threaded upper end, and
    the first apertures are threaded to receive the threaded upper end of the bone screws.

11. The maxillary expander of claim 1, wherein:
    the bone screws comprise a threaded upper end, and
    the first apertures are threaded to receive the threaded upper end of the bone screws.

12. The maxillary expander of claim 11, wherein:
    each of the first bodies comprises 3 of the first apertures and 2 of the second apertures, and
    each of the second bodies comprises 2 of the third apertures.

13. The maxillary expander of claim 1, wherein the adjustment mechanism comprises a telescopic expansion screw.

14. The maxillary expander of claim 13, wherein:
    each of the first bodies comprises 3 of the first apertures and 2 of the second apertures, and
    each of the second bodies comprises 2 of the third apertures.

15. The maxillary expander of claim 1, wherein the adjustment mechanism is an expansion screw having threads at only one end.

16. The maxillary expander of claim 15, wherein:
    each of the first bodies comprises 3 of the first apertures and 2 of the second apertures, and
    each of the second bodies comprises 2 of the third apertures.

17. The maxillary expander of claim 15, wherein:
    the bone screws comprise a threaded upper end, and
    the first apertures are threaded to receive the threaded upper end of the bone screws.

18. The maxillary expander of claim 1, wherein the maxillary expander is configured so that force is not applied to the teeth of the patient.

19. The maxillary expander of claim 18, wherein:
    each of the first bodies comprises 3 of the first apertures and 2 of the second apertures, and
    each of the second bodies comprises 2 of the third apertures.

20. The maxillary expander of claim 18, wherein:
    the bone screws comprise a threaded upper end, and
    the first apertures are threaded to receive the threaded upper end of the bone screws.

* * * * *